(12) United States Patent
    Joshi et al.

(10) Patent No.: US 12,602,775 B2
(45) Date of Patent: Apr. 14, 2026

(54) INTERPOLATION OF MEDICAL IMAGES

(71) Applicant: GLOBUS MEDICAL, INC., Audubon, PA (US)

(72) Inventors: Sanjay M. Joshi, Andover, MA (US); Arjang Noushin, Nashua, NH (US); Neil Crawford, Chandler, AZ (US)

(73) Assignee: Globus Medical Inc., Audubon, PA (US)

( * ) Notice: Subject to any disclaimer, the term of this patent is extended or adjusted under 35 U.S.C. 154(b) by 574 days.

(21) Appl. No.: 17/742,463

(22) Filed: May 12, 2022

(65) Prior Publication Data

US 2023/0368330 A1    Nov. 16, 2023

(51) Int. Cl.
    *G06T 7/00*      (2017.01)
    *A61B 34/20*     (2016.01)
    *G06T 3/10*      (2024.01)
    *G06T 7/55*      (2017.01)
    *G06T 7/73*      (2017.01)
    (Continued)

(52) U.S. Cl.
    CPC ............ *G06T 7/0012* (2013.01); *A61B 34/20* (2016.02); *G06T 3/10* (2024.01); *G06T 7/55* (2017.01); *G06T 7/73* (2017.01); *G06T 17/20* (2013.01); *G06V 10/26* (2022.01); *A61B 2034/2055* (2016.02); *G06T 2207/10081* (2013.01); *G06T 2207/10088* (2013.01); *G06T 2207/10116* (2013.01); *G06T 2207/20081* (2013.01); *G06T 2207/20084* (2013.01)

(58) Field of Classification Search
    None
    See application file for complete search history.

(56) References Cited

U.S. PATENT DOCUMENTS

| | | | |
|---|---|---|---|
| 4,150,293 A | 4/1979 | Franke | |
| 5,246,010 A | 9/1993 | Gazzara et al. | |
| 5,354,314 A | 10/1994 | Hardy et al. | |

(Continued)

FOREIGN PATENT DOCUMENTS

CN          111667469 A  *  9/2020  ........... G06F 18/241

OTHER PUBLICATIONS

US 8,231,638 B2, 07/2012, Swarup et al. (withdrawn)

(Continued)

*Primary Examiner* — Michelle M Entezari Hausmann

(57)                ABSTRACT

A system can be configured to generate a medical image. The system can include processing circuitry and memory coupled to the processing circuitry. The memory can include instructions stored therein that are executable by the processing circuitry to cause the system to perform operations. The operations can include obtaining a first image of an anatomical object. The operations can further include extracting first information associated with the anatomical object from the first image. The operations can further include obtaining a second image of the anatomical object. The operations can further include extracting second information associated with the anatomical object from the second image. The operations can further include generating the medical image based on the first information, the second information, and predetermined information. The predetermined information can be associated with images of anatomical objects of a type that is a type of the anatomical object.

12 Claims, 12 Drawing Sheets

(51) Int. Cl.
  *G06T 17/20*     (2006.01)
  *G06V 10/26*     (2022.01)

(56)                    References Cited

U.S. PATENT DOCUMENTS

| | | | |
|---|---|---|---|
| 5,397,323 | A | 3/1995 | Taylor et al. |
| 5,598,453 | A | 1/1997 | Baba et al. |
| 5,772,594 | A | 6/1998 | Barrick |
| 5,791,908 | A | 8/1998 | Gillio |
| 5,820,559 | A | 10/1998 | Ng et al. |
| 5,825,982 | A | 10/1998 | Wright et al. |
| 5,887,121 | A | 3/1999 | Funda et al. |
| 5,911,449 | A | 6/1999 | Daniele et al. |
| 5,951,475 | A | 9/1999 | Gueziec et al. |
| 5,987,960 | A | 11/1999 | Messner et al. |
| 6,012,216 | A | 1/2000 | Esteves et al. |
| 6,031,888 | A | 2/2000 | Ivan et al. |
| 6,033,415 | A | 3/2000 | Mittelstadt et al. |
| 6,080,181 | A | 6/2000 | Jensen et al. |
| 6,106,511 | A | 8/2000 | Jensen |
| 6,122,541 | A | 9/2000 | Cosman et al. |
| 6,144,875 | A | 11/2000 | Schweikard et al. |
| 6,157,853 | A | 12/2000 | Blume et al. |
| 6,167,145 | A | 12/2000 | Foley et al. |
| 6,167,292 | A | 12/2000 | Badano et al. |
| 6,201,984 | B1 | 3/2001 | Funda et al. |
| 6,203,196 | B1 | 3/2001 | Meyer et al. |
| 6,205,411 | B1 | 3/2001 | DiGioia, III et al. |
| 6,212,419 | B1 | 4/2001 | Blume et al. |
| 6,231,565 | B1 | 5/2001 | Tovey et al. |
| 6,236,875 | B1 | 5/2001 | Bucholz et al. |
| 6,246,900 | B1 | 6/2001 | Cosman et al. |
| 6,301,495 | B1 | 10/2001 | Gueziec et al. |
| 6,306,126 | B1 | 10/2001 | Montezuma |
| 6,312,435 | B1 | 11/2001 | Wallace et al. |
| 6,314,311 | B1 | 11/2001 | Williams et al. |
| 6,320,929 | B1 | 11/2001 | Von Der Haar |
| 6,322,567 | B1 | 11/2001 | Mittelstadt et al. |
| 6,325,808 | B1 | 12/2001 | Bernard et al. |
| 6,340,363 | B1 | 1/2002 | Bolger et al. |
| 6,377,011 | B1 | 4/2002 | Ben-Ur |
| 6,379,302 | B1 | 4/2002 | Kessman et al. |
| 6,402,762 | B2 | 6/2002 | Hunter et al. |
| 6,424,885 | B1 | 7/2002 | Niemeyer et al. |
| 6,447,503 | B1 | 9/2002 | Wynne et al. |
| 6,451,027 | B1 | 9/2002 | Cooper et al. |
| 6,477,400 | B1 | 11/2002 | Barrick |
| 6,484,049 | B1 | 11/2002 | Seeley et al. |
| 6,487,267 | B1 | 11/2002 | Wolter |
| 6,490,467 | B1 | 12/2002 | Bucholz et al. |
| 6,490,475 | B1 | 12/2002 | Seeley et al. |
| 6,499,488 | B1 | 12/2002 | Hunter et al. |
| 6,501,981 | B1 | 12/2002 | Schweikard et al. |
| 6,507,751 | B2 | 1/2003 | Blume et al. |
| 6,535,756 | B1 | 3/2003 | Simon et al. |
| 6,560,354 | B1 | 5/2003 | Maurer, Jr. et al. |
| 6,565,554 | B1 | 5/2003 | Niemeyer |
| 6,587,750 | B2 | 7/2003 | Gerbi et al. |
| 6,614,453 | B1 | 9/2003 | Suri et al. |
| 6,614,871 | B1 | 9/2003 | Kobiki et al. |
| 6,619,840 | B2 | 9/2003 | Rasche et al. |
| 6,636,757 | B1 | 10/2003 | Jascob et al. |
| 6,645,196 | B1 | 11/2003 | Nixon et al. |
| 6,666,579 | B2 | 12/2003 | Jensen |
| 6,669,635 | B2 | 12/2003 | Kessman et al. |
| 6,701,173 | B2 | 3/2004 | Nowinski et al. |
| 6,757,068 | B2 | 6/2004 | Foxlin |
| 6,782,287 | B2 | 8/2004 | Grzeszczuk et al. |
| 6,783,524 | B2 | 8/2004 | Anderson et al. |
| 6,786,896 | B1 | 9/2004 | Madhani et al. |
| 6,788,018 | B1 | 9/2004 | Blumenkranz |
| 6,804,581 | B2 | 10/2004 | Wang et al. |
| 6,823,207 | B1 | 11/2004 | Jensen et al. |
| 6,827,351 | B2 | 12/2004 | Graziani et al. |
| 6,837,892 | B2 | 1/2005 | Shoham |
| 6,839,612 | B2 | 1/2005 | Sanchez et al. |
| 6,856,826 | B2 | 2/2005 | Seeley et al. |
| 6,856,827 | B2 | 2/2005 | Seeley et al. |
| 6,879,880 | B2 | 4/2005 | Nowlin et al. |
| 6,892,090 | B2 | 5/2005 | Verard et al. |
| 6,920,347 | B2 | 7/2005 | Simon et al. |
| 6,922,632 | B2 | 7/2005 | Foxlin |
| 6,968,224 | B2 | 11/2005 | Kessman et al. |
| 6,978,166 | B2 | 12/2005 | Foley et al. |
| 6,988,009 | B2 | 1/2006 | Grimm et al. |
| 6,991,627 | B2 | 1/2006 | Madhani et al. |
| 6,996,487 | B2 | 2/2006 | Jutras et al. |
| 6,999,852 | B2 | 2/2006 | Green |
| 7,007,699 | B2 | 3/2006 | Martinelli et al. |
| 7,016,457 | B1 | 3/2006 | Senzig et al. |
| 7,043,961 | B2 | 5/2006 | Pandey et al. |
| 7,062,006 | B1 | 6/2006 | Pelc et al. |
| 7,063,705 | B2 | 6/2006 | Young et al. |
| 7,072,707 | B2 | 7/2006 | Galloway, Jr. et al. |
| 7,083,615 | B2 | 8/2006 | Peterson et al. |
| 7,097,640 | B2 | 8/2006 | Wang et al. |
| 7,099,428 | B2 | 8/2006 | Clinthorne et al. |
| 7,108,421 | B2 | 9/2006 | Gregerson et al. |
| 7,130,676 | B2 | 10/2006 | Barrick |
| 7,139,418 | B2 | 11/2006 | Abovitz et al. |
| 7,139,601 | B2 | 11/2006 | Bucholz et al. |
| 7,155,316 | B2 | 12/2006 | Sutherland et al. |
| 7,164,968 | B2 | 1/2007 | Treat et al. |
| 7,167,738 | B2 | 1/2007 | Schweikard et al. |
| 7,169,141 | B2 | 1/2007 | Brock et al. |
| 7,172,627 | B2 | 2/2007 | Fiere et al. |
| 7,194,120 | B2 | 3/2007 | Wicker et al. |
| 7,197,107 | B2 | 3/2007 | Arai et al. |
| 7,231,014 | B2 | 6/2007 | Levy |
| 7,231,063 | B2 | 6/2007 | Naimark et al. |
| 7,239,940 | B2 | 7/2007 | Wang et al. |
| 7,248,914 | B2 | 7/2007 | Hastings et al. |
| 7,301,648 | B2 | 11/2007 | Foxlin |
| 7,302,288 | B1 | 11/2007 | Schellenberg |
| 7,313,430 | B2 | 12/2007 | Urquhart et al. |
| 7,318,805 | B2 | 1/2008 | Schweikard et al. |
| 7,318,827 | B2 | 1/2008 | Leitner et al. |
| 7,319,897 | B2 | 1/2008 | Leitner et al. |
| 7,324,623 | B2 | 1/2008 | Heuscher et al. |
| 7,327,865 | B2 | 2/2008 | Fu et al. |
| 7,331,967 | B2 | 2/2008 | Lee et al. |
| 7,333,642 | B2 | 2/2008 | Green |
| 7,339,341 | B2 | 3/2008 | Oleynikov et al. |
| 7,366,562 | B2 | 4/2008 | Dukesherer et al. |
| 7,379,790 | B2 | 5/2008 | Toth et al. |
| 7,386,365 | B2 | 6/2008 | Nixon |
| 7,422,592 | B2 | 9/2008 | Morley et al. |
| 7,435,216 | B2 | 10/2008 | Kwon et al. |
| 7,440,793 | B2 | 10/2008 | Chauhan et al. |
| 7,460,637 | B2 | 12/2008 | Clinthorne et al. |
| 7,466,303 | B2 | 12/2008 | Yi et al. |
| 7,493,153 | B2 | 2/2009 | Ahmed et al. |
| 7,505,617 | B2 | 3/2009 | Fu et al. |
| 7,533,892 | B2 | 5/2009 | Schena et al. |
| 7,542,791 | B2 | 6/2009 | Mire et al. |
| 7,555,331 | B2 | 6/2009 | Viswanathan |
| 7,567,834 | B2 | 7/2009 | Clayton et al. |
| 7,594,912 | B2 | 9/2009 | Cooper et al. |
| 7,606,613 | B2 | 10/2009 | Simon et al. |
| 7,607,440 | B2 | 10/2009 | Coste-Maniere et al. |
| 7,623,902 | B2 | 11/2009 | Pacheco |
| 7,630,752 | B2 | 12/2009 | Viswanathan |
| 7,630,753 | B2 | 12/2009 | Simon et al. |
| 7,643,862 | B2 | 1/2010 | Schoenefeld |
| 7,660,623 | B2 | 2/2010 | Hunter et al. |
| 7,661,881 | B2 | 2/2010 | Gregerson et al. |
| 7,683,331 | B2 | 3/2010 | Chang |
| 7,683,332 | B2 | 3/2010 | Chang |
| 7,689,320 | B2 | 3/2010 | Prisco et al. |
| 7,691,098 | B2 | 4/2010 | Wallace et al. |
| 7,702,379 | B2 | 4/2010 | Avinash et al. |
| 7,702,477 | B2 | 4/2010 | Tuemmler et al. |
| 7,711,083 | B2 | 5/2010 | Heigl et al. |
| 7,711,406 | B2 | 5/2010 | Kuhn et al. |

(56) References Cited

U.S. PATENT DOCUMENTS

| | | | |
|---|---|---|---|
| 7,720,523 | B2 | 5/2010 | Omernick et al. |
| 7,725,253 | B2 | 5/2010 | Foxlin |
| 7,726,171 | B2 | 6/2010 | Langlotz et al. |
| 7,742,801 | B2 | 6/2010 | Neubauer et al. |
| 7,751,865 | B2 | 7/2010 | Jascob et al. |
| 7,760,849 | B2 | 7/2010 | Zhang |
| 7,762,825 | B2 | 7/2010 | Burbank et al. |
| 7,763,015 | B2 | 7/2010 | Cooper et al. |
| 7,787,699 | B2 | 8/2010 | Mahesh et al. |
| 7,796,728 | B2 | 9/2010 | Bergfjord |
| 7,813,838 | B2 | 10/2010 | Sommer |
| 7,818,044 | B2 | 10/2010 | Dukesherer et al. |
| 7,819,859 | B2 | 10/2010 | Prisco et al. |
| 7,824,401 | B2 | 11/2010 | Manzo et al. |
| 7,831,294 | B2 | 11/2010 | Viswanathan |
| 7,834,484 | B2 | 11/2010 | Sartor |
| 7,835,557 | B2 | 11/2010 | Kendrick et al. |
| 7,835,778 | B2 | 11/2010 | Foley et al. |
| 7,835,784 | B2 | 11/2010 | Mire et al. |
| 7,840,253 | B2 | 11/2010 | Tremblay et al. |
| 7,840,256 | B2 | 11/2010 | Lakin et al. |
| 7,843,158 | B2 | 11/2010 | Prisco |
| 7,844,320 | B2 | 11/2010 | Shahidi |
| 7,853,305 | B2 | 12/2010 | Simon et al. |
| 7,853,313 | B2 | 12/2010 | Thompson |
| 7,865,269 | B2 | 1/2011 | Prisco et al. |
| D631,966 | S | 2/2011 | Perloff et al. |
| 7,879,045 | B2 | 2/2011 | Gielen et al. |
| 7,881,767 | B2 | 2/2011 | Strommer et al. |
| 7,881,770 | B2 | 2/2011 | Melkent et al. |
| 7,886,743 | B2 | 2/2011 | Cooper et al. |
| RE42,194 | E | 3/2011 | Foley et al. |
| RE42,226 | E | 3/2011 | Foley et al. |
| 7,900,524 | B2 | 3/2011 | Calloway et al. |
| 7,907,166 | B2 | 3/2011 | Lamprecht et al. |
| 7,909,122 | B2 | 3/2011 | Schena et al. |
| 7,925,653 | B2 | 4/2011 | Saptharishi |
| 7,930,065 | B2 | 4/2011 | Larkin et al. |
| 7,935,130 | B2 | 5/2011 | Williams |
| 7,940,999 | B2 | 5/2011 | Liao et al. |
| 7,945,012 | B2 | 5/2011 | Ye et al. |
| 7,945,021 | B2 | 5/2011 | Shapiro et al. |
| 7,953,470 | B2 | 5/2011 | Vetter et al. |
| 7,954,397 | B2 | 6/2011 | Choi et al. |
| 7,971,341 | B2 | 7/2011 | Dukesherer et al. |
| 7,974,674 | B2 | 7/2011 | Hauck et al. |
| 7,974,677 | B2 | 7/2011 | Mire et al. |
| 7,974,681 | B2 | 7/2011 | Wallace et al. |
| 7,979,157 | B2 | 7/2011 | Anvari |
| 7,983,733 | B2 | 7/2011 | Viswanathan |
| 7,988,215 | B2 | 8/2011 | Seibold |
| 7,996,110 | B2 | 8/2011 | Lipow et al. |
| 8,004,121 | B2 | 8/2011 | Sartor |
| 8,004,229 | B2 | 8/2011 | Nowlin et al. |
| 8,010,177 | B2 | 8/2011 | Csavoy et al. |
| 8,019,045 | B2 | 9/2011 | Kato |
| 8,021,310 | B2 | 9/2011 | Sanborn et al. |
| 8,035,685 | B2 | 10/2011 | Jensen |
| 8,046,054 | B2 | 10/2011 | Kim et al. |
| 8,046,057 | B2 | 10/2011 | Clarke |
| 8,052,688 | B2 | 11/2011 | Wolf, II |
| 8,054,184 | B2 | 11/2011 | Cline et al. |
| 8,054,752 | B2 | 11/2011 | Druke et al. |
| 8,057,397 | B2 | 11/2011 | Li et al. |
| 8,057,407 | B2 | 11/2011 | Martinelli et al. |
| 8,062,288 | B2 | 11/2011 | Cooper et al. |
| 8,062,375 | B2 | 11/2011 | Glerum et al. |
| 8,066,524 | B2 | 11/2011 | Burbank et al. |
| 8,073,335 | B2 | 12/2011 | Labonville et al. |
| 8,079,950 | B2 | 12/2011 | Stern et al. |
| 8,086,299 | B2 | 12/2011 | Adler et al. |
| 8,092,370 | B2 | 1/2012 | Roberts et al. |
| 8,098,914 | B2 | 1/2012 | Liao et al. |
| 8,100,950 | B2 | 1/2012 | St. Clair et al. |
| 8,105,320 | B2 | 1/2012 | Manzo |
| 8,108,025 | B2 | 1/2012 | Csavoy et al. |
| 8,109,877 | B2 | 2/2012 | Moctezuma de la Barrera et al. |
| 8,112,292 | B2 | 2/2012 | Simon |
| 8,116,430 | B1 | 2/2012 | Shapiro et al. |
| 8,120,301 | B2 | 2/2012 | Goldberg et al. |
| 8,121,249 | B2 | 2/2012 | Wang et al. |
| 8,123,675 | B2 | 2/2012 | Funda et al. |
| 8,133,229 | B1 | 3/2012 | Bonutti |
| 8,142,420 | B2 | 3/2012 | Schena |
| 8,147,494 | B2 | 4/2012 | Leitner et al. |
| 8,150,494 | B2 | 4/2012 | Simon et al. |
| 8,150,497 | B2 | 4/2012 | Gielen et al. |
| 8,150,498 | B2 | 4/2012 | Gielen et al. |
| 8,165,658 | B2 | 4/2012 | Waynik et al. |
| 8,170,313 | B2 | 5/2012 | Kendrick et al. |
| 8,179,073 | B2 | 5/2012 | Farritor et al. |
| 8,182,476 | B2 | 5/2012 | Julian et al. |
| 8,184,880 | B2 | 5/2012 | Zhao et al. |
| 8,202,278 | B2 | 6/2012 | Orban, III et al. |
| 8,208,708 | B2 | 6/2012 | Homan et al. |
| 8,208,988 | B2 | 6/2012 | Jenser |
| 8,219,177 | B2 | 7/2012 | Smith et al. |
| 8,219,178 | B2 | 7/2012 | Smith et al. |
| 8,220,468 | B2 | 7/2012 | Cooper et al. |
| 8,224,024 | B2 | 7/2012 | Foxlin et al. |
| 8,224,484 | B2 | 7/2012 | Swarup et al. |
| 8,225,798 | B2 | 7/2012 | Baldwin et al. |
| 8,228,368 | B2 | 7/2012 | Zhao et al. |
| 8,231,610 | B2 | 7/2012 | Jo et al. |
| 8,239,001 | B2 | 8/2012 | Verard et al. |
| 8,241,271 | B2 | 8/2012 | Millman et al. |
| 8,248,413 | B2 | 8/2012 | Gattani et al. |
| 8,256,319 | B2 | 9/2012 | Cooper et al. |
| 8,263,933 | B2 | 9/2012 | Zeile |
| 8,271,069 | B2 | 9/2012 | Jascob et al. |
| 8,271,130 | B2 | 9/2012 | Hourtash |
| 8,281,670 | B2 | 10/2012 | Larkin et al. |
| 8,282,653 | B2 | 10/2012 | Nelson et al. |
| 8,301,226 | B2 | 10/2012 | Csavoy et al. |
| 8,311,611 | B2 | 11/2012 | Csavoy et al. |
| 8,320,991 | B2 | 11/2012 | Jascob et al. |
| 8,332,012 | B2 | 12/2012 | Kienzle, III |
| 8,333,755 | B2 | 12/2012 | Cooper et al. |
| 8,335,552 | B2 | 12/2012 | Stiles |
| 8,335,557 | B2 | 12/2012 | Maschke |
| 8,348,931 | B2 | 1/2013 | Cooper et al. |
| 8,353,963 | B2 | 1/2013 | Glerum |
| 8,358,818 | B2 | 1/2013 | Miga et al. |
| 8,359,730 | B2 | 1/2013 | Burg et al. |
| 8,374,673 | B2 | 2/2013 | Adcox et al. |
| 8,374,723 | B2 | 2/2013 | Zhao et al. |
| 8,379,791 | B2 | 2/2013 | Forthmann et al. |
| 8,386,019 | B2 | 2/2013 | Camus et al. |
| 8,392,022 | B2 | 3/2013 | Ortmaier et al. |
| 8,394,099 | B2 | 3/2013 | Patwardhan |
| 8,395,342 | B2 | 3/2013 | Prisco |
| 8,398,634 | B2 | 3/2013 | Manzo et al. |
| 8,400,094 | B2 | 3/2013 | Schena |
| 8,414,957 | B2 | 4/2013 | Enzerink et al. |
| 8,418,073 | B2 | 4/2013 | Mohr et al. |
| 8,450,694 | B2 | 5/2013 | Baviera et al. |
| 8,452,447 | B2 | 5/2013 | Nixon |
| RE44,305 | E | 6/2013 | Foley et al. |
| 8,462,911 | B2 | 6/2013 | Vesel et al. |
| 8,465,476 | B2 | 6/2013 | Rogers et al. |
| 8,465,771 | B2 | 6/2013 | Wan et al. |
| 8,467,851 | B2 | 6/2013 | Mire et al. |
| 8,467,852 | B2 | 6/2013 | Csavoy et al. |
| 8,469,947 | B2 | 6/2013 | Devengenzo et al. |
| RE44,392 | E | 7/2013 | Hynes |
| 8,483,434 | B2 | 7/2013 | Buehner et al. |
| 8,483,800 | B2 | 7/2013 | Jensen et al. |
| 8,486,532 | B2 | 7/2013 | Enzerink et al. |
| 8,489,235 | B2 | 7/2013 | Moll et al. |
| 8,500,722 | B2 | 8/2013 | Cooper |
| 8,500,728 | B2 | 8/2013 | Newton et al. |
| 8,504,201 | B2 | 8/2013 | Moll et al. |
| 8,506,555 | B2 | 8/2013 | Ruiz Morales |
| 8,506,556 | B2 | 8/2013 | Schena |

(56)         References Cited

U.S. PATENT DOCUMENTS

| | | | |
|---|---|---|---|
| 8,508,173 | B2 | 8/2013 | Goldberg et al. |
| 8,512,318 | B2 | 8/2013 | Tovey et al. |
| 8,515,576 | B2 | 8/2013 | Lipow et al. |
| 8,518,120 | B2 | 8/2013 | Glerum et al. |
| 8,521,331 | B2 | 8/2013 | Itkowitz |
| 8,526,688 | B2 | 9/2013 | Groszmann et al. |
| 8,526,700 | B2 | 9/2013 | Issacs |
| 8,527,094 | B2 | 9/2013 | Kumar et al. |
| 8,528,440 | B2 | 9/2013 | Morley et al. |
| 8,532,741 | B2 | 9/2013 | Heruth et al. |
| 8,541,970 | B2 | 9/2013 | Nowlin et al. |
| 8,548,563 | B2 | 10/2013 | Simon et al. |
| 8,549,732 | B2 | 10/2013 | Burg et al. |
| 8,551,114 | B2 | 10/2013 | Ramos de la Pena |
| 8,551,116 | B2 | 10/2013 | Julian et al. |
| 8,556,807 | B2 | 10/2013 | Scott et al. |
| 8,556,979 | B2 | 10/2013 | Glerum et al. |
| 8,560,118 | B2 | 10/2013 | Green et al. |
| 8,561,473 | B2 | 10/2013 | Blumenkranz |
| 8,562,594 | B2 | 10/2013 | Cooper et al. |
| 8,571,638 | B2 | 10/2013 | Shoham |
| 8,571,710 | B2 | 10/2013 | Coste-Maniere et al. |
| 8,573,465 | B2 | 11/2013 | Shelton, IV |
| 8,574,303 | B2 | 11/2013 | Sharkey et al. |
| 8,585,420 | B2 | 11/2013 | Burbank et al. |
| 8,594,841 | B2 | 11/2013 | Zhao et al. |
| 8,597,198 | B2 | 12/2013 | Sanborn et al. |
| 8,600,478 | B2 | 12/2013 | Verard et al. |
| 8,603,077 | B2 | 12/2013 | Cooper et al. |
| 8,605,096 | B2 * | 12/2013 | Visser .................... G06V 20/47 |
| | | | 345/475 |
| 8,611,985 | B2 | 12/2013 | Lavallee et al. |
| 8,613,230 | B2 | 12/2013 | Blumenkranz et al. |
| 8,621,939 | B2 | 1/2014 | Blumenkranz et al. |
| 8,624,537 | B2 | 1/2014 | Nowlin et al. |
| 8,630,389 | B2 | 1/2014 | Kato |
| 8,634,897 | B2 | 1/2014 | Simon et al. |
| 8,634,957 | B2 | 1/2014 | Toth et al. |
| 8,638,056 | B2 | 1/2014 | Goldberg et al. |
| 8,638,057 | B2 | 1/2014 | Goldberg et al. |
| 8,639,000 | B2 | 1/2014 | Zhao et al. |
| 8,641,726 | B2 | 2/2014 | Bonutti |
| 8,644,907 | B2 | 2/2014 | Hartmann et al. |
| 8,657,809 | B2 | 2/2014 | Schoepp |
| 8,660,635 | B2 | 2/2014 | Simon et al. |
| 8,666,544 | B2 | 3/2014 | Moll et al. |
| 8,675,939 | B2 | 3/2014 | Moctezuma de la Barrera |
| 8,678,647 | B2 | 3/2014 | Gregerson et al. |
| 8,679,125 | B2 | 3/2014 | Smith et al. |
| 8,679,183 | B2 | 3/2014 | Glerum et al. |
| 8,682,413 | B2 | 3/2014 | Lloyd |
| 8,684,253 | B2 | 4/2014 | Giordano et al. |
| 8,685,098 | B2 | 4/2014 | Glerum et al. |
| 8,693,730 | B2 | 4/2014 | Umasuthan et al. |
| 8,694,075 | B2 | 4/2014 | Groszmann et al. |
| 8,696,458 | B2 | 4/2014 | Foxlin et al. |
| 8,700,123 | B2 | 4/2014 | Okamura et al. |
| 8,706,086 | B2 | 4/2014 | Glerum |
| 8,706,185 | B2 | 4/2014 | Foley et al. |
| 8,706,301 | B2 | 4/2014 | Zhao et al. |
| 8,717,430 | B2 | 5/2014 | Simon et al. |
| 8,727,618 | B2 | 5/2014 | Maschke et al. |
| 8,734,432 | B2 | 5/2014 | Tuma et al. |
| 8,738,115 | B2 | 5/2014 | Amberg et al. |
| 8,738,181 | B2 | 5/2014 | Greer et al. |
| 8,740,882 | B2 | 6/2014 | Jun et al. |
| 8,746,252 | B2 | 6/2014 | McGrogan et al. |
| 8,749,189 | B2 | 6/2014 | Nowlin et al. |
| 8,749,190 | B2 | 6/2014 | Nowlin et al. |
| 8,761,930 | B2 | 6/2014 | Nixon |
| 8,764,448 | B2 | 7/2014 | Yang et al. |
| 8,771,170 | B2 | 7/2014 | Mesallum et al. |
| 8,781,186 | B2 | 7/2014 | Clements et al. |
| 8,781,630 | B2 | 7/2014 | Banks et al. |
| 8,784,385 | B2 | 7/2014 | Boyden et al. |
| 8,786,241 | B2 | 7/2014 | Nowlin et al. |
| 8,787,520 | B2 | 7/2014 | Baba |
| 8,792,704 | B2 | 7/2014 | Isaacs |
| 8,798,231 | B2 | 8/2014 | Notohara et al. |
| 8,800,838 | B2 | 8/2014 | Shelton, IV |
| 8,808,164 | B2 | 8/2014 | Hoffman et al. |
| 8,812,077 | B2 | 8/2014 | Dempsey |
| 8,814,793 | B2 | 8/2014 | Brabrand |
| 8,816,628 | B2 | 8/2014 | Nowlin et al. |
| 8,818,105 | B2 | 8/2014 | Myronenko et al. |
| 8,820,605 | B2 | 9/2014 | Shelton, IV |
| 8,821,511 | B2 | 9/2014 | Von Jako et al. |
| 8,823,308 | B2 | 9/2014 | Nowlin et al. |
| 8,827,996 | B2 | 9/2014 | Scott et al. |
| 8,828,024 | B2 | 9/2014 | Farritor et al. |
| 8,830,224 | B2 | 9/2014 | Zhao et al. |
| 8,834,489 | B2 | 9/2014 | Cooper et al. |
| 8,834,490 | B2 | 9/2014 | Bonutti |
| 8,838,270 | B2 | 9/2014 | Druke et al. |
| 8,844,789 | B2 | 9/2014 | Shelton, IV et al. |
| 8,855,822 | B2 | 10/2014 | Bartol et al. |
| 8,858,598 | B2 | 10/2014 | Seifert et al. |
| 8,860,753 | B2 | 10/2014 | Bhandarkar et al. |
| 8,864,751 | B2 | 10/2014 | Prisco et al. |
| 8,864,798 | B2 | 10/2014 | Weiman et al. |
| 8,864,833 | B2 | 10/2014 | Glerum et al. |
| 8,867,703 | B2 | 10/2014 | Shapiro et al. |
| 8,870,880 | B2 | 10/2014 | Himmelberger et al. |
| 8,876,866 | B2 | 11/2014 | Zappacosta et al. |
| 8,880,223 | B2 | 11/2014 | Raj et al. |
| 8,882,803 | B2 | 11/2014 | Iott et al. |
| 8,883,210 | B1 | 11/2014 | Truncale et al. |
| 8,888,821 | B2 | 11/2014 | Rezach et al. |
| 8,888,853 | B2 | 11/2014 | Glerum et al. |
| 8,888,854 | B2 | 11/2014 | Glerum et al. |
| 8,894,652 | B2 | 11/2014 | Seifert et al. |
| 8,894,688 | B2 | 11/2014 | Suh |
| 8,894,691 | B2 | 11/2014 | Iott et al. |
| 8,906,069 | B2 | 12/2014 | Hansell et al. |
| 8,964,934 | B2 | 2/2015 | Ein-Gal |
| 8,992,580 | B2 | 3/2015 | Bar et al. |
| 8,996,169 | B2 | 3/2015 | Lightcap et al. |
| 9,001,963 | B2 | 4/2015 | Sowards-Emmerd et al. |
| 9,002,076 | B2 | 4/2015 | Khadem et al. |
| 9,044,190 | B2 | 6/2015 | Rubner et al. |
| 9,107,683 | B2 | 8/2015 | Hourtash et al. |
| 9,125,556 | B2 | 9/2015 | Zehavi et al. |
| 9,131,986 | B2 | 9/2015 | Greer et al. |
| 9,215,968 | B2 | 12/2015 | Schostek et al. |
| 9,308,050 | B2 | 4/2016 | Kostrzewski et al. |
| 9,380,984 | B2 | 7/2016 | Li et al. |
| 9,393,039 | B2 | 7/2016 | Lechner et al. |
| 9,398,886 | B2 | 7/2016 | Gregerson et al. |
| 9,398,890 | B2 | 7/2016 | Dong et al. |
| 9,414,859 | B2 | 8/2016 | Ballard et al. |
| 9,420,975 | B2 | 8/2016 | Gutfleisch et al. |
| 9,492,235 | B2 | 11/2016 | Hourtash et al. |
| 9,592,096 | B2 | 3/2017 | Maillet et al. |
| 9,750,465 | B2 | 9/2017 | Engel et al. |
| 9,757,203 | B2 | 9/2017 | Hourtash et al. |
| 9,767,557 | B1 * | 9/2017 | Gulsun .................. G06V 10/82 |
| 9,795,354 | B2 | 10/2017 | Menegaz et al. |
| 9,814,535 | B2 | 11/2017 | Bar et al. |
| 9,820,783 | B2 | 11/2017 | Donner et al. |
| 9,833,265 | B2 | 12/2017 | Donner et al. |
| 9,848,922 | B2 | 12/2017 | Tohmeh et al. |
| 9,925,011 | B2 | 3/2018 | Gombert et al. |
| 9,931,025 | B1 | 4/2018 | Graetzel et al. |
| 10,034,717 | B2 | 7/2018 | Miller et al. |
| 12,094,114 | B2 * | 9/2024 | Wang .................... G06V 10/25 |
| 2001/0036302 | A1 | 11/2001 | Miller |
| 2002/0035321 | A1 | 3/2002 | Bucholz et al. |
| 2004/0068172 | A1 | 4/2004 | Nowinski et al. |
| 2004/0076259 | A1 | 4/2004 | Jensen et al. |
| 2005/0096502 | A1 | 5/2005 | Khalili |
| 2005/0143651 | A1 | 6/2005 | Verard et al. |
| 2005/0171558 | A1 | 8/2005 | Abovitz et al. |
| 2006/0100610 | A1 | 5/2006 | Wallace et al. |
| 2006/0173329 | A1 | 8/2006 | Marquart et al. |

(56) References Cited

U.S. PATENT DOCUMENTS

| | | |
|---|---|---|
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | von Jako |
| 2008/0109012 A1 | 5/2008 | Falco et al. |
| 2008/0144906 A1 | 6/2008 | Allred et al. |
| 2008/0161680 A1 | 7/2008 | von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |

(56) References Cited

U.S. PATENT DOCUMENTS

| | | | |
|---|---|---|---|
| 2014/0100587 A1 | 4/2014 | Farritor et al. | |
| 2014/0121676 A1 | 5/2014 | Kostrzewski et al. | |
| 2014/0128882 A1 | 5/2014 | Kwak et al. | |
| 2014/0130810 A1 | 5/2014 | Azizian et al. | |
| 2014/0135796 A1 | 5/2014 | Simon et al. | |
| 2014/0142591 A1 | 5/2014 | Alvarez et al. | |
| 2014/0142592 A1 | 5/2014 | Moon et al. | |
| 2014/0148692 A1 | 5/2014 | Hartmann et al. | |
| 2014/0163581 A1 | 6/2014 | Devengenzo et al. | |
| 2014/0171781 A1 | 6/2014 | Stiles | |
| 2014/0171900 A1 | 6/2014 | Stiles | |
| 2014/0171965 A1 | 6/2014 | Loh et al. | |
| 2014/0180308 A1 | 6/2014 | von Grunberg | |
| 2014/0180309 A1 | 6/2014 | Seeber et al. | |
| 2014/0187915 A1 | 7/2014 | Yaroshenko et al. | |
| 2014/0188132 A1 | 7/2014 | Kang | |
| 2014/0194699 A1 | 7/2014 | Roh et al. | |
| 2014/0221819 A1 | 8/2014 | Sarment | |
| 2014/0222023 A1 | 8/2014 | Kim et al. | |
| 2014/0228631 A1 | 8/2014 | Kwak et al. | |
| 2014/0234804 A1 | 8/2014 | Huang et al. | |
| 2014/0257328 A1 | 9/2014 | Kim et al. | |
| 2014/0257329 A1 | 9/2014 | Jang et al. | |
| 2014/0257330 A1 | 9/2014 | Choi et al. | |
| 2014/0275760 A1 | 9/2014 | Lee et al. | |
| 2014/0275985 A1 | 9/2014 | Walker et al. | |
| 2014/0276931 A1 | 9/2014 | Parihar et al. | |
| 2014/0276940 A1 | 9/2014 | Seo | |
| 2014/0276944 A1 | 9/2014 | Farritor et al. | |
| 2014/0288413 A1 | 9/2014 | Hwang et al. | |
| 2014/0299648 A1 | 10/2014 | Shelton, IV et al. | |
| 2014/0303434 A1 | 10/2014 | Farritor et al. | |
| 2014/0303643 A1 | 10/2014 | Ha et al. | |
| 2014/0305995 A1 | 10/2014 | Shelton, IV et al. | |
| 2014/0309659 A1 | 10/2014 | Roh et al. | |
| 2014/0316436 A1 | 10/2014 | Bar et al. | |
| 2014/0323803 A1 | 10/2014 | Hoffman et al. | |
| 2014/0324070 A1 | 10/2014 | Min et al. | |
| 2014/0330288 A1 | 11/2014 | Date et al. | |
| 2014/0333775 A1* | 11/2014 | Naikal | H04N 21/44008 |
| | | | 348/159 |
| 2014/0364720 A1 | 12/2014 | Darrow et al. | |
| 2014/0371577 A1 | 12/2014 | Maillet et al. | |
| 2015/0039034 A1 | 2/2015 | Frankel et al. | |
| 2015/0085970 A1 | 3/2015 | Bouhnik et al. | |
| 2015/0146847 A1 | 5/2015 | Liu | |
| 2015/0150524 A1 | 6/2015 | Yorkston et al. | |
| 2015/0196261 A1 | 7/2015 | Funk | |
| 2015/0213633 A1 | 7/2015 | Chang et al. | |
| 2015/0335480 A1 | 11/2015 | Alvarez et al. | |
| 2015/0342647 A1 | 12/2015 | Frankel et al. | |
| 2016/0005194 A1 | 1/2016 | Schretter et al. | |
| 2016/0166329 A1 | 6/2016 | Langan et al. | |
| 2016/0235480 A1 | 8/2016 | Scholl et al. | |
| 2016/0249990 A1 | 9/2016 | Glozman et al. | |
| 2016/0302871 A1 | 10/2016 | Gregerson et al. | |
| 2016/0320322 A1 | 11/2016 | Suzuki | |
| 2016/0331335 A1 | 11/2016 | Gregerson et al. | |
| 2017/0135770 A1 | 5/2017 | Scholl et al. | |
| 2017/0143284 A1 | 5/2017 | Sehnert et al. | |
| 2017/0143426 A1 | 5/2017 | Isaacs et al. | |
| 2017/0156816 A1 | 6/2017 | Ibrahim | |
| 2017/0202629 A1 | 7/2017 | Maillet et al. | |
| 2017/0212723 A1 | 7/2017 | Atarot et al. | |
| 2017/0215825 A1 | 8/2017 | Johnson et al. | |
| 2017/0215826 A1 | 8/2017 | Johnson et al. | |
| 2017/0215827 A1 | 8/2017 | Johnson et al. | |
| 2017/0231710 A1 | 8/2017 | Scholl et al. | |
| 2017/0258426 A1 | 9/2017 | Risher-Kelly et al. | |
| 2017/0273748 A1 | 9/2017 | Hourtash et al. | |
| 2017/0296277 A1 | 10/2017 | Hourtash et al. | |
| 2017/0360493 A1 | 12/2017 | Zucher et al. | |
| 2022/0183760 A1* | 6/2022 | Fouts | G16H 20/40 |
| 2022/0296303 A1* | 9/2022 | McLeod | A61B 8/5261 |
| 2023/0118864 A1* | 4/2023 | Zhang | G06V 10/26 |
| | | | 382/103 |
| 2023/0144433 A1* | 5/2023 | Zhang | G06N 3/0464 |
| | | | 382/157 |
| 2023/0200930 A1* | 6/2023 | Liu | A61B 5/0066 |
| | | | 606/1 |
| 2023/0274492 A1* | 8/2023 | Chen | G06T 17/00 |
| | | | 345/419 |
| 2024/0331354 A1* | 10/2024 | Azad | G16H 20/40 |

OTHER PUBLICATIONS

Jeong, Yongwon, and Richard J. Radke. "Modeling inter-and intra-patient anatomical variation using a bilinear model." 2006 Conference on Computer Vision and Pattern Recognition Workshop (CVPRW'06). IEEE, 2006. (Year: 2006).*
CN 111667469 A [Machine Translation] (Year: 2020).*

* cited by examiner

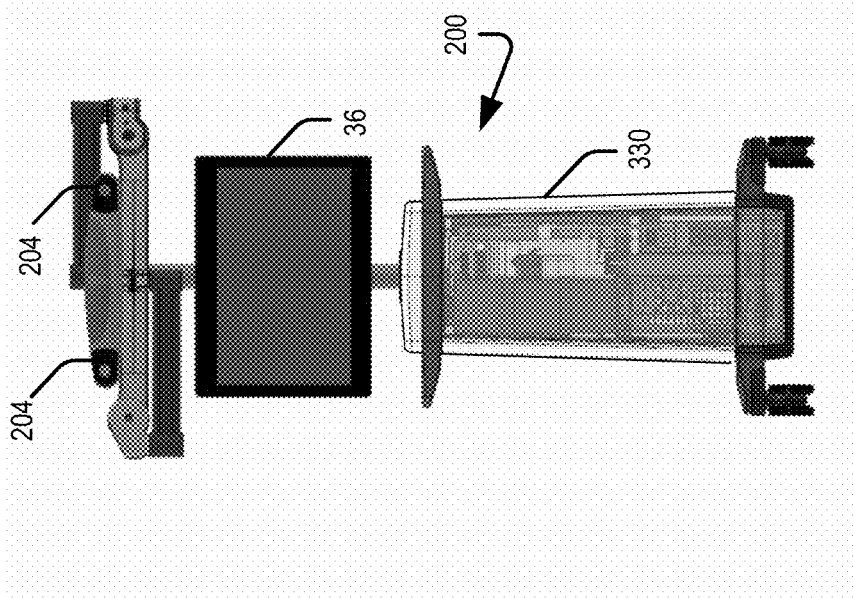
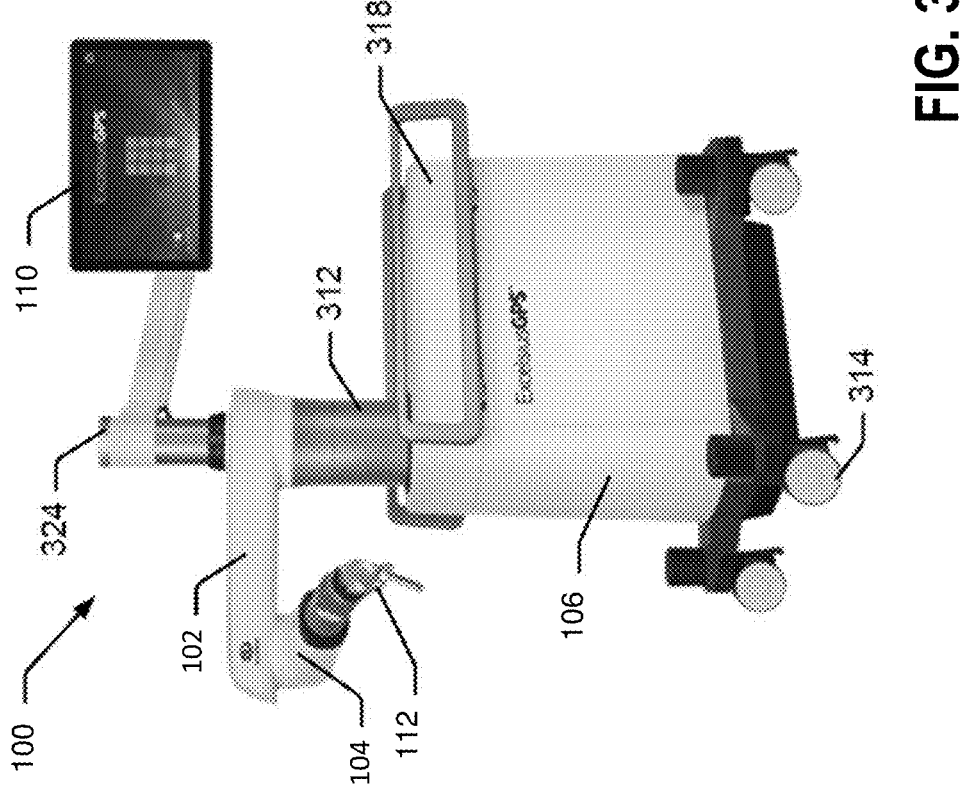
FIG. 3

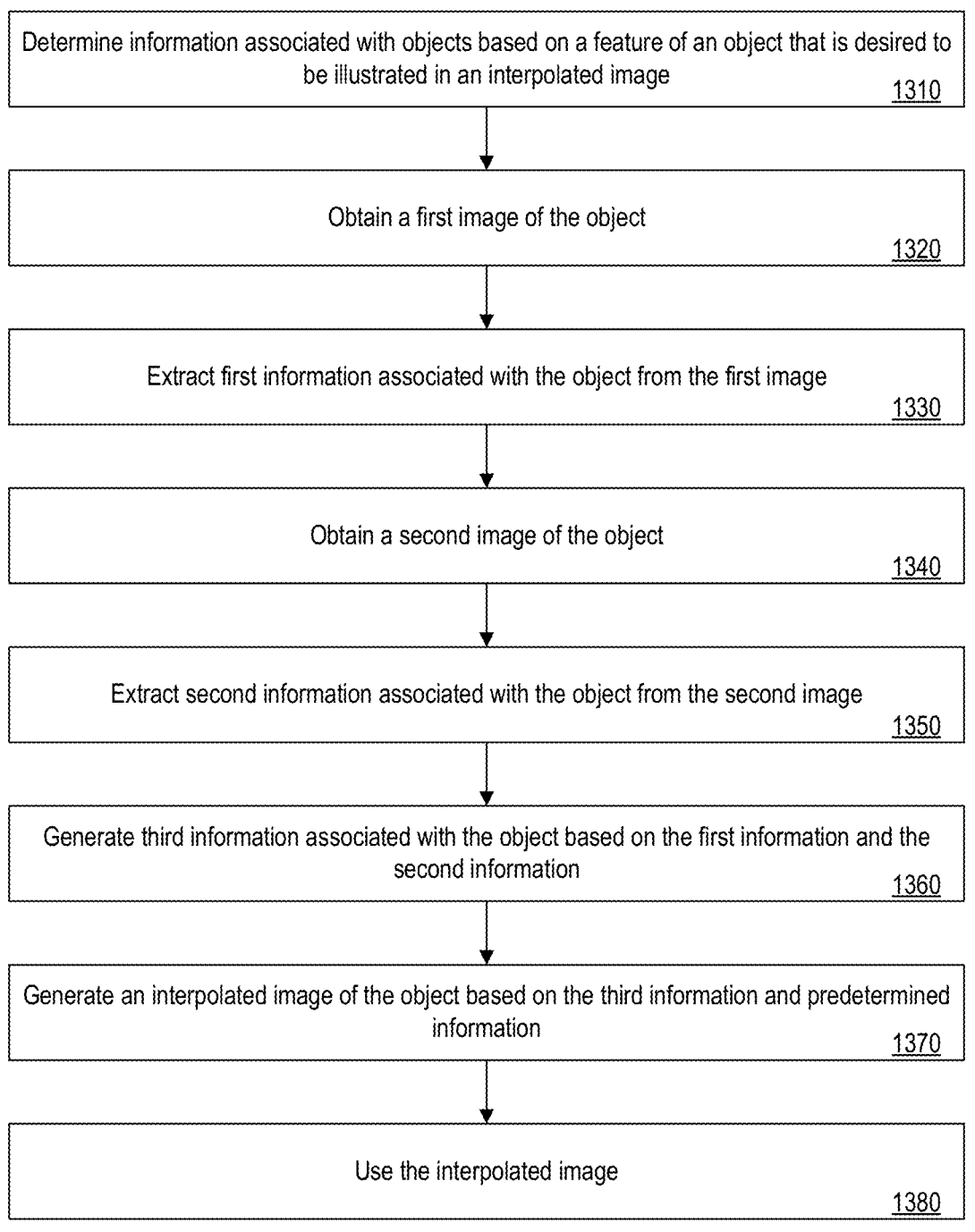

Determine information associated with objects based on a feature of an object that is desired to be illustrated in an interpolated image

1310

Obtain a first image of the object

1320

Extract first information associated with the object from the first image

1330

Obtain a second image of the object

1340

Extract second information associated with the object from the second image

1350

Generate third information associated with the object based on the first information and the second information

1360

Generate an interpolated image of the object based on the third information and predetermined information

1370

Use the interpolated image

INTERPOLATION OF MEDICAL IMAGES

FIELD

The present disclosure relates to medical devices and systems, and more particularly, medical imaging systems interpolating medical images.

BACKGROUND

Surgical operating rooms can contain a diverse range of medical equipment, which can include computer assisted surgical navigation systems, medical imaging devices (e.g., computerized tomography ("CT") scanners, fluoroscopy imaging, etc.), and surgical robots.

A computer assisted surgical navigation system can provide a surgeon with computerized visualization of the present pose of a surgical tool relative to medical images of a patient's anatomy. Camera tracking systems for computer assisted surgical navigation typically use a set of cameras to track pose of a reference array on a surgical tool, which is being positioned by a surgeon during surgery, relative to a patient reference array (also "dynamic reference base" ("DRB")) attached to a patient. The reference arrays allow the camera tracking system to determine a pose of the surgical tool relative to anatomical structure imaged by a medical image of the patient and relative to the patient. The surgeon can thereby use real-time visual feedback of the pose to navigate the surgical tool during a surgical procedure on the patient.

Many surgical workflows using computer assisted surgical navigation systems require image scans, such as CT scans or magnetic resonance imaging scans, during the surgical procedure. Perpendicular scan slices (axial, sagittal, and coronal) may be used to enable operators to visualize the patient's anatomy alongside the relative poses of surgical instruments. Obtaining accurate medical images can require precise placement of an imaging system (e.g., an x-ray emitter, an x-ray detector, and a camera), which may not be determinable outside of a guess-and-check procedure. In some examples, this can lead to settling for sub-optimal medical images, which may negatively impact the success of a medical procedure. In additional or alternative examples, obtaining accurate medical images requires a large number of pictures (e.g., scans) to be taken which can present a challenge for surgeons and other surgical team members under the time constraints and other pressures of a surgery environment. Furthermore, the imaging systems can be expensive and in-high demand such that it is desirable to reduce the time spent using the imaging system. Moreover, some imaging systems result in a radiation exposure for the patient such that it is desirable to reduce the radiation exposure for the patient. Some embodiments herein describe improved imaging systems that reduce the number of images that need to be taken to obtain an accurate medical image.

SUMMARY

Some embodiments of the present disclosure are directed to interpolating an image based on an interpolated content vector and a predefined style vector.

In some embodiments, a system configured to generate a medical image is provided. The system comprises processing circuitry and memory coupled to the processing circuitry. The memory has instructions stored therein that are executable by the processing circuitry to cause the system to perform operations. The operations include obtaining a first image of an anatomical object. The operations further include extracting first information associated with the anatomical object from the first image. The operations further include obtaining a second image of the anatomical object. The operations further include extracting second information associated with the anatomical object from the second image. The operations further include generating the medical image based on the first information, the second information, and predetermined information that is associated with images of anatomical objects of a type that is a type of the anatomical object.

In other embodiments, a system of generating an interpolated image of an object is provided. The system comprises processing circuitry and memory coupled to the processing circuitry. The memory has instructions stored therein that are executable by the processing circuitry to cause the system to perform operations. The operations include obtaining a first image of the object. The operations further include extracting first information associated with the object from the first image. The operations further include obtaining a second image of the object. The operations further include extracting second information associated with the object from the second image. The operations further include generating third information associated with the object based on the first information and the second information. The operations further include generating the interpolated image of the object based on the third information and predetermined information associated with objects. The objects and the object are of a same type.

In other embodiments, a medical imaging system configured to generate a medical image is provided. The medical imaging system includes processing circuitry and memory coupled to the processing circuitry. The memory has instructions stored therein that are executable by the processing circuitry to cause the medical imaging system to perform operations. The operations include obtaining a first content vector associated with a first image of an anatomical object. The operations further include obtaining a second content vector associated with a second image of the anatomical object. The operations further include interpolating a third content vector based on the first content vector and the third content vector. The operations further include generating the medical image based on the third content vector and a predetermined style vector that is associated with medical images of anatomical objects.

Other systems and corresponding methods and computer program products according to embodiments of the inventive subject matter will be or become apparent to one with skill in the art upon review of the following drawings and detailed description. It is intended that all such additional systems, methods. and computer program products be included within this description, be within the scope of the present inventive subject matter, and be protected by the accompanying claims. Moreover, it is intended that all embodiments disclosed herein can be implemented separately or combined in any way and/or combination.

DESCRIPTION OF THE DRAWINGS

Aspects of the present disclosure are illustrated by way of example and are not limited by the accompanying drawings. In the drawings:

FIG. 3 further illustrates the camera tracking system and the surgical robot configured according to some embodiments;

FIGS. 13-14 are flow charts illustrating examples of operations performed by a system according to some embodiments.

DETAILED DESCRIPTION

Figure 1:
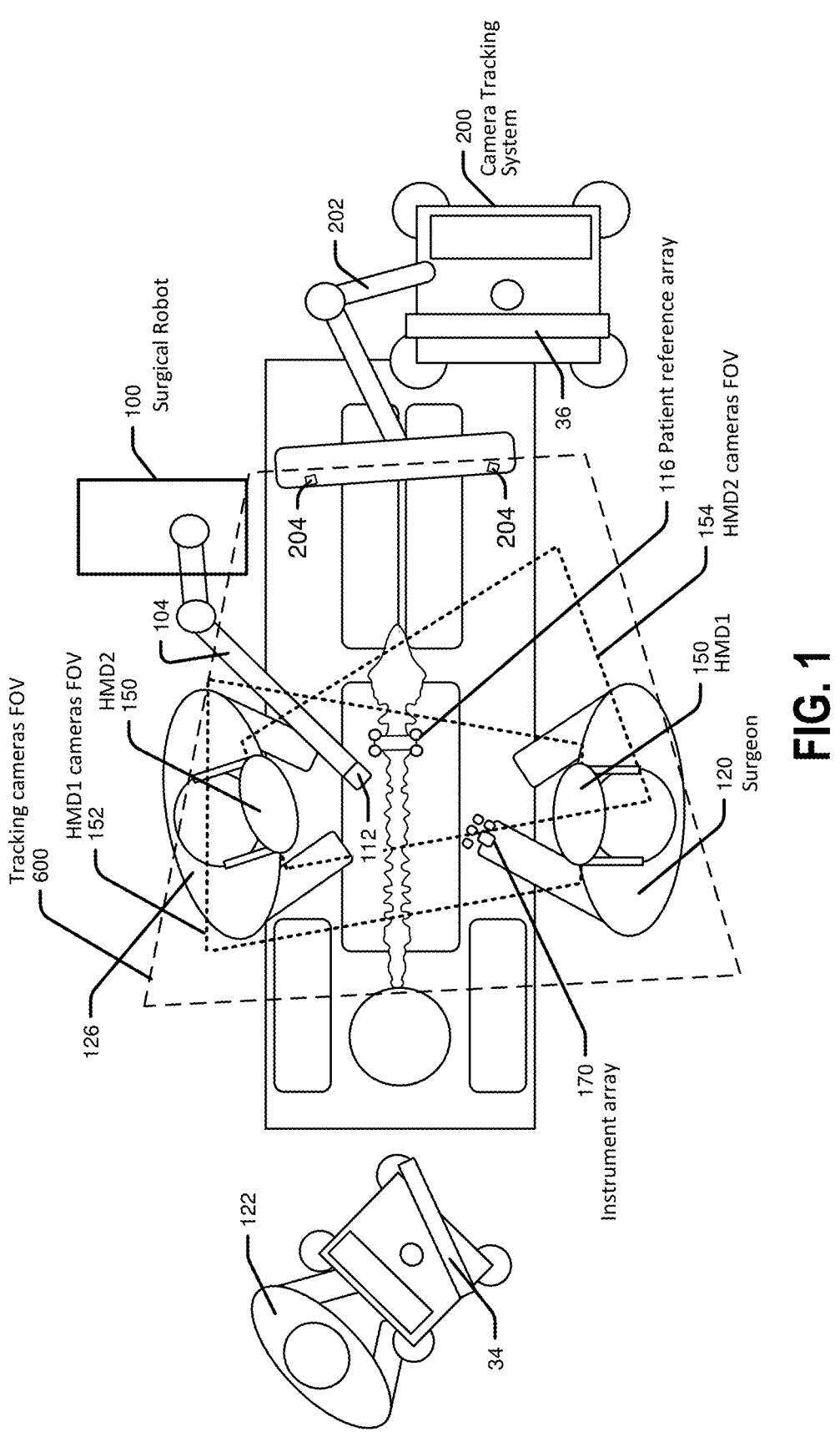
FIG. 1 is an overhead view of personnel wearing extended reality (XR) headsets during a surgical procedure in a surgical room that includes a camera tracking system for navigated surgery and which may further include a surgical robot for robotic assistance according to some embodiments.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Various embodiments of the present disclosure are directed to generating medical images based on interpolated content vectors and a globally-optimized style vector. Before describing these embodiments is detail, various components that may be used for performing embodiments in a navigated surgery system are described with reference to FIGS. 1-7.

Figure 2:
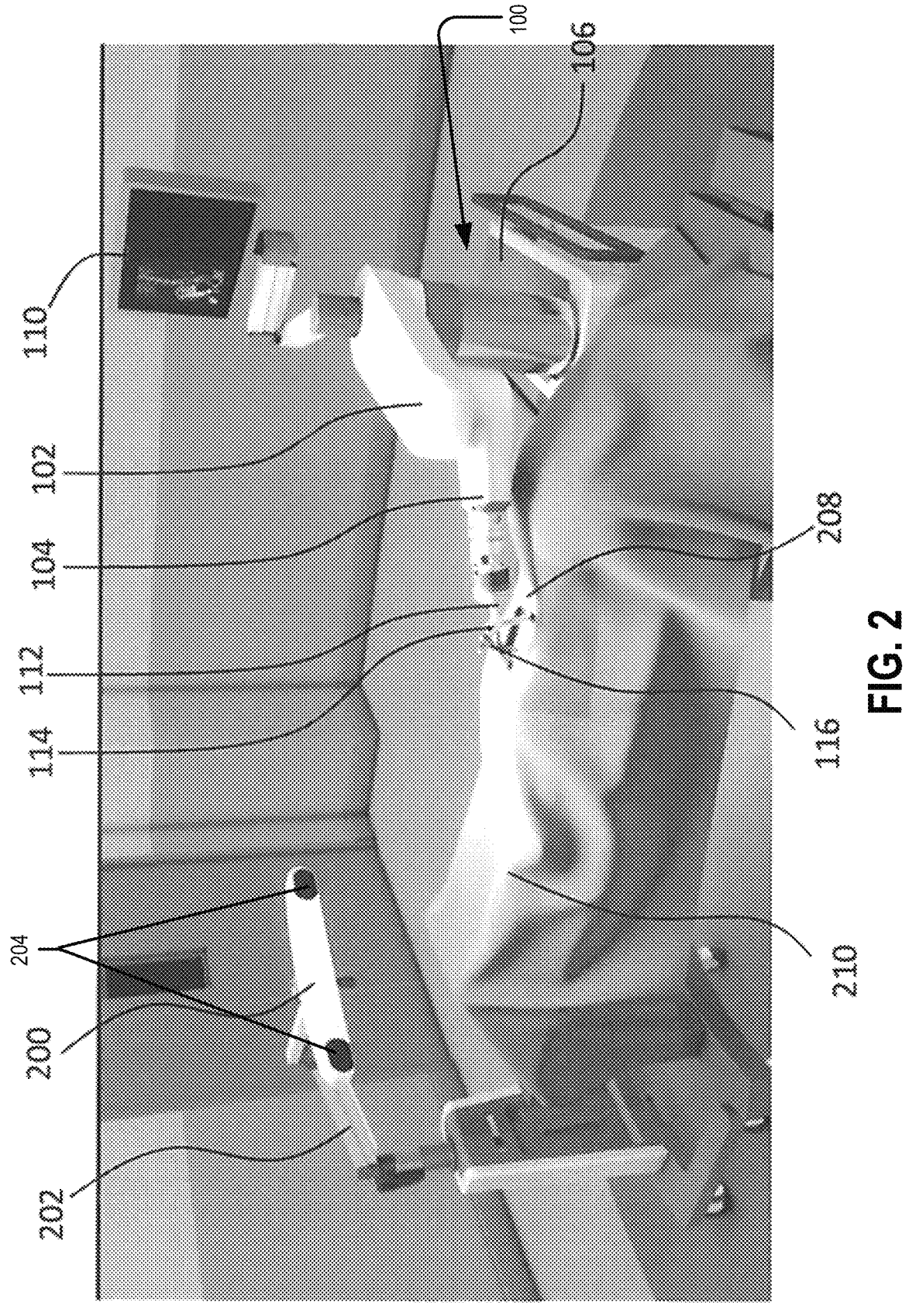
FIG. 2 illustrates the camera tracking system and the surgical robot positioned relative to a patient according to some embodiments.
Figure 4:
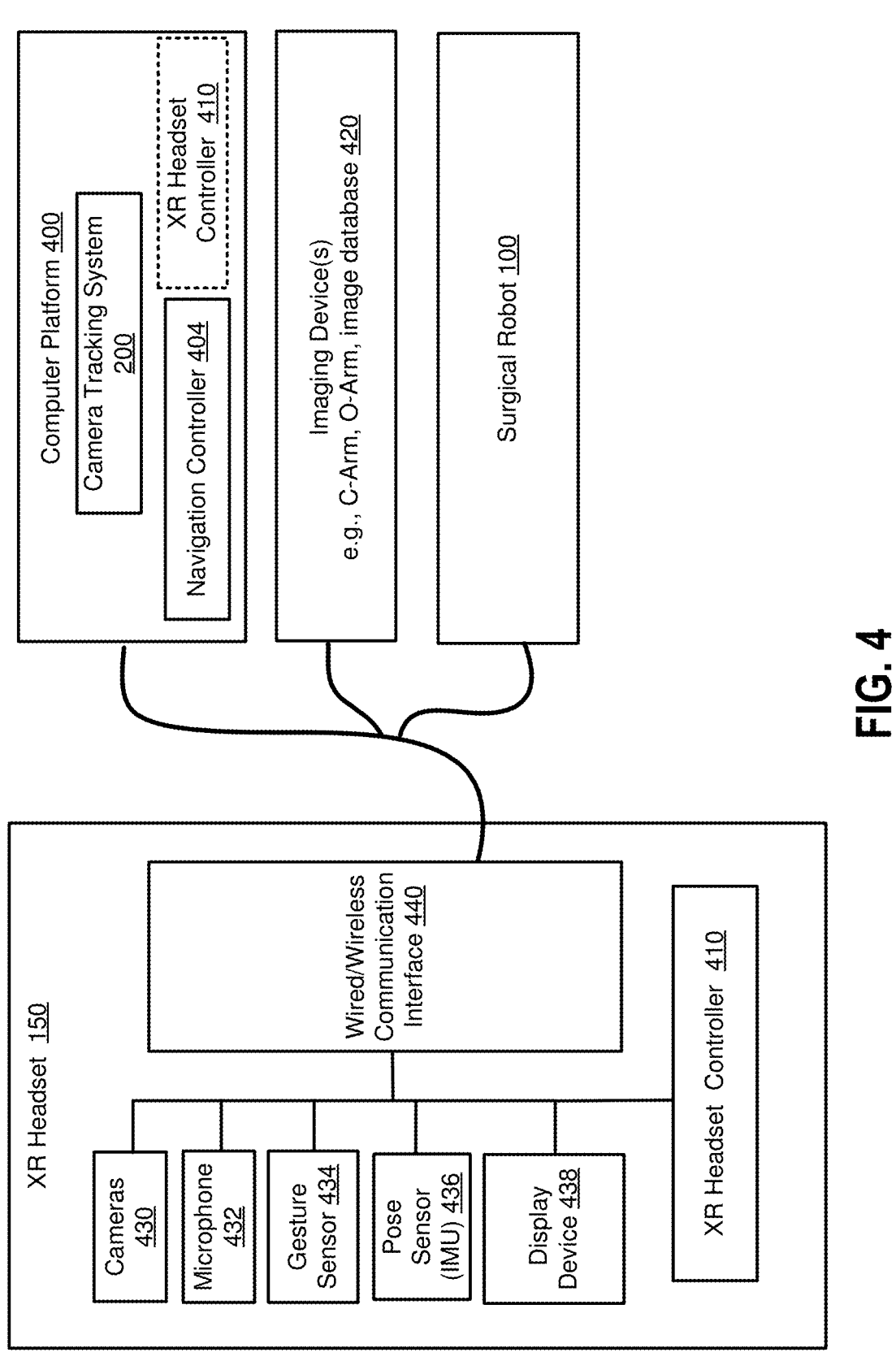
FIG. 4 illustrates a block diagram of a surgical system that includes an XR headset, a computer platform, imaging devices, and a surgical robot which are configured to operate according to some embodiments.
Figure 5:
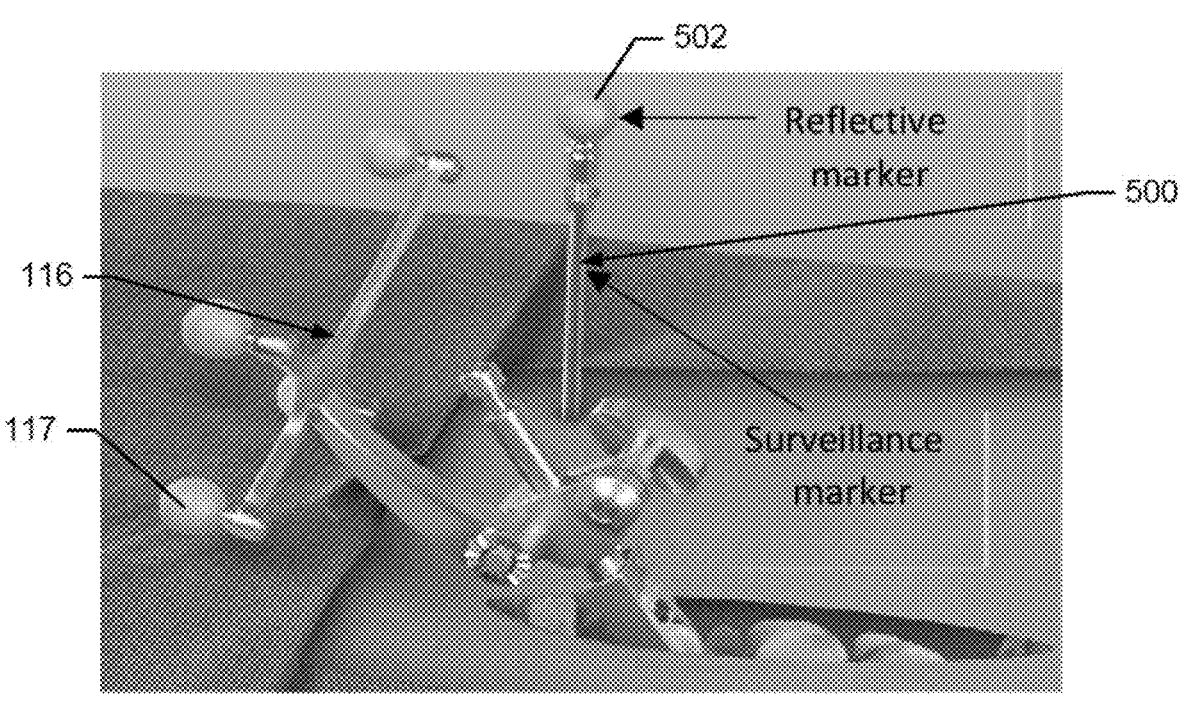
FIG. 5 illustrates a patient reference array (DRB) and a surveillance marker.

FIG. 1 is an overhead view of personnel wearing extended reality ("XR") headsets 150 during a surgical procedure in a surgical room that includes a camera tracking system 200 for navigated surgery during a surgical procedure and which may further include a surgical robot 100 for robotic assistance, according to some embodiments. FIG. 2 illustrates the camera tracking system 200 and the surgical robot 100 positioned relative to a patient, according to some embodiments. FIG. 3 further illustrates the camera tracking system 200 and the surgical robot 100 configured according to some embodiments. FIG. 4 illustrates a block diagram of a surgical system that includes an XR headset 150, a computer platform 400, imaging devices 420, and the surgical robot 100 which are configured to operate according to some embodiments. FIG. 5 illustrates a patient reference array 116 (also "dynamic reference base" ("DRB")) and a surveillance marker 500.

The XR headset 150 may be configured to augment a real-world scene with computer generated XR images. The XR headset 150 may be configured to provide an augmented reality ("AR") viewing environment by displaying the computer generated XR images on a see-through display screen that allows light from the real-world scene to pass therethrough for combined viewing by the user. Alternatively, the XR headset 150 may be configured to provide a virtual reality ("VR") viewing environment by preventing or substantially preventing light from the real-world scene from being directly viewed by the user while the user is viewing the computer-generated AR images on a display screen. The XR headset 150 can be configured to provide both AR and VR viewing environments. Thus, the term XR headset can referred to as an AR headset or a VR headset.

Referring to FIGS. 1-7, the surgical robot 100 may include, for example, one or more robot arms 104, a display 110, an end-effector 112, for example, including a guide tube 114, and an end effector reference array which can include one or more tracking markers. A patient reference array 116 ("DRB") has a plurality of tracking markers 117 and is secured directly to the patient 210 (e.g., to a bone of the patient 210). A spaced apart surveillance marker 500 (FIG. 5) has a single marker 502 connected to a shaft that is secured directly to the patient 210 at a spaced apart location from the patient reference array 116. Another reference array 170 is attached or formed on an instrument, surgical tool, surgical implant device, etc.

The camera tracking system 200 includes tracking cameras 204 which may be spaced apart stereo cameras configured with partially overlapping field-of-views. The camera tracking system 200 can have any suitable configuration of arm(s) 202 to move, orient, and support the tracking cameras 204 in a desired location, and may contain at least one processor operable to track location of an individual marker and pose of an array of markers. As used herein, the term "pose" refers to the location (e.g., along 3 orthogonal axes)

and/or the rotation angle (e.g., about the 3 orthogonal axes) of markers (e.g., DRB) relative to another marker (e.g., surveillance marker) and/or to a defined coordinate system (e.g., camera coordinate system). A pose may therefore be defined based on only the multidimensional location of the markers relative to another marker and/or relative to the defined coordinate system, based on only the multidimensional rotational angles of the markers relative to the other marker and/or to the defined coordinate system, or based on a combination of the multidimensional location and the multidimensional rotational angles. The term "pose" therefore is used to refer to location, rotational angle, or combination thereof.

The tracking cameras 204 may include, e.g., infrared cameras (e.g., bifocal or stereophotogrammetric cameras), operable to identify, for example, active and passive tracking markers for single markers (e.g., surveillance marker 500) and reference arrays which can be formed on or attached to the patient 210 (e.g., patient reference array, DRB), end effector 112 (e.g., end effector reference array), XR headset (s) 150 worn by a surgeon 120 and/or a surgical assistant 126, etc. in a given measurement volume of a camera coordinate system while viewable from the perspective of the tracking cameras 204. The tracking cameras 204 may scan the given measurement volume and detect light that is emitted or reflected from the markers in order to identify and determine locations of individual markers and poses of the reference arrays in three-dimensions. For example, active reference arrays may include infrared-emitting markers that are activated by an electrical signal (e.g., infrared light emitting diodes ("LEDs")), and passive reference arrays may include retro-reflective markers that reflect infrared light (e.g., they reflect incoming IR radiation into the direction of the incoming light), for example, emitted by illuminators on the tracking cameras 204 or other suitable device.

The XR headsets 150 may each include tracking cameras (e.g., spaced apart stereo cameras) that can track location of a surveillance marker and poses of reference arrays within the XR camera headset field-of-views ("FOVs") 152 and 154, respectively. Accordingly, as illustrated in FIG. 1, the location of the surveillance marker and the poses of reference arrays on various objects can be tracked while in the FOVs 152 and 154 of the XR headsets 150 and/or a FOV 600 of the tracking cameras 204.

FIGS. 1-2 illustrate a potential configuration for the placement of the camera tracking system 200 and the surgical robot 100 in an operating room environment. Computer-aided navigated surgery can be provided by the camera tracking system controlling the XR headsets 150 and/or other displays 34, 36, and 110 to display surgical procedure navigation information. The surgical robot 100 is optional during computer-aided navigated surgery.

The camera tracking system 200 may operate using tracking information and other information provided by multiple XR headsets 150 such as inertial tracking information and optical tracking information (frames of tracking data). The XR headsets 150 operate to display visual information and may play-out audio information to the wearer. This information can be from local sources (e.g., the surgical robot 100 and/or other medical), remote sources (e.g., patient medical image server), and/or other electronic equipment. The camera tracking system 200 may track markers in 6 degrees-of-freedom ("6DOF") relative to three axes of a 3D coordinate system and rotational angles about each axis. The XR headsets 150 may also operate to track hand poses and gestures to enable gesture-based interactions with "virtual" buttons and interfaces displayed through the XR headsets 150 and can also interpret hand or finger pointing or gesturing as various defined commands. Additionally, the XR headsets 150 may have a 1-10× magnification digital color camera sensor called a digital loupe. In some embodiments, one or more of the XR headsets 150 are minimalistic XR headsets that display local or remote information but include fewer sensors and are therefore more lightweight.

An "outside-in" machine vision navigation bar supports the tracking cameras 204 and may include a color camera. The machine vision navigation bar generally has a more stable view of the environment because it does not move as often or as quickly as the XR headsets 150 while positioned on wearers' heads. The patient reference array 116 (DRB) is generally rigidly attached to the patient with stable pitch and roll relative to gravity. This local rigid patient reference 116 can serve as a common reference for reference frames relative to other tracked arrays, such as a reference array on the end effector 112, instrument reference array 170, and reference arrays on the XR headsets 150.

During a surgical procedure using surgical navigation, the surveillance marker 500 is affixed to the patient to provide information on whether the patient reference array 116 has shifted. For example, during a spinal fusion procedure with planned placement of pedicle screw fixation, two small incisions are made over the posterior superior iliac spine bilaterally. The DRB and the surveillance marker are then affixed to the posterior superior iliac spine bilaterally. If the surveillance marker's 500 location changes relative to the patient reference array 116, the camera tracking system 200 may display a meter indicating the amount of movement and/or may display a pop-up warning message to inform the user that the patient reference array may have been bumped. If the patient reference array has indeed been bumped, the registration of the patient reference array to the tracked coordinate system may be invalid and could result in erroneous navigation which is off target.

When present, the surgical robot (also "robot") may be positioned near or next to patient 210. The robot 100 can be positioned at any suitable location near the patient 210 depending on the area of the patient 210 undergoing the surgical procedure. The camera tracking system 200 may be separated from the robot system 100 and positioned at the foot of patient 210. This location allows the tracking camera 200 to have a direct visual line of sight to the surgical area 208. In the configuration shown, the surgeon 120 may be positioned across from the robot 100, but is still able to manipulate the end-effector 112 and the display 110. A surgical assistant 126 may be positioned across from the surgeon 120 again with access to both the end-effector 112 and the display 110. If desired, the locations of the surgeon 120 and the assistant 126 may be reversed. An anesthesiologist 122, nurse or scrub tech can operate equipment which may be connected to display information from the camera tracking system 200 on a display 34.

With respect to the other components of the robot 100, the display 110 can be attached to the surgical robot 100 or in a remote location. End-effector 112 may be coupled to the robot arm 104 and controlled by at least one motor. In some embodiments, end-effector 112 can comprise a guide tube 114, which is configured to receive and orient a surgical instrument, tool, or implant used to perform a surgical procedure on the patient 210.

As used herein, the term "end-effector" is used interchangeably with the terms "end-effectuator" and "effectuator element." The term "instrument" is used in a non-limiting manner and can be used interchangeably with "tool" and "implant" to generally refer to any type of device that can be used during a surgical procedure in accordance with embodiments disclosed herein. Example instruments, tools, and implants include, without limitation, drills, screwdrivers, saws, dilators, retractors, probes, implant inserters, and implant devices such as a screws, spacers, interbody fusion devices, plates, rods, etc. Although generally shown with a guide tube 114, it will be appreciated that the end-effector 112 may be replaced with any suitable instrumentation suitable for use in surgery. In some embodiments, end-effector 112 can comprise any known structure for effecting the movement of the surgical instrument in a desired manner.

The surgical robot 100 is operable to control the translation and orientation of the end-effector 112. The robot 100 may move the end-effector 112 under computer control along x-, y-, and z-axes, for example. The end-effector 112 can be configured for selective rotation about one or more of the x-, y-, and z-axis, and a Z Frame axis, such that one or more of the Euler Angles (e.g., roll, pitch, and/or yaw) associated with end-effector 112 can be selectively computer controlled. In some embodiments, selective control of the translation and orientation of end-effector 112 can permit performance of medical procedures with significantly improved accuracy compared to conventional robots that utilize, for example, a 6DOF robot arm comprising only rotational axes. For example, the surgical robot 100 may be used to operate on patient 210, and robot arm 104 can be positioned above the body of patient 210, with end-effector 112 selectively angled relative to the z-axis toward the body of patient 210.

In some example embodiments, the XR headsets 150 can be controlled to dynamically display an updated graphical indication of the pose of the surgical instrument so that the user can be aware of the pose of the surgical instrument at all times during the procedure.

In some further embodiments, surgical robot 100 can be operable to correct the path of a surgical instrument guided by the robot arm 104 if the surgical instrument strays from the selected, preplanned trajectory. The surgical robot 100 can be operable to permit stoppage, modification, and/or manual control of the movement of end-effector 112 and/or the surgical instrument. Thus, in use, a surgeon or other user can use the surgical robot 100 as part of computer assisted navigated surgery, and has the option to stop, modify, or manually control the autonomous or semi-autonomous movement of the end-effector 112 and/or the surgical instrument.

Reference arrays of markers can be formed on or connected to robot arms 102 and/or 104, the end-effector 112 (e.g., end-effector array 114 in FIG. 2), and/or a surgical instrument (e.g., instrument array 170) to track poses in 6DOF along 3 orthogonal axes and rotation about the axes. The reference arrays enable each of the marked objects (e.g., the end-effector 112, the patient 210, and the surgical instruments) to be tracked by the tracking camera 200, and the tracked poses can be used to provide navigated guidance during a surgical procedure and/or used to control movement of the surgical robot 100 for guiding the end-effector 112 and/or an instrument manipulated by the end-effector 112.

Referring to FIG. 3 the surgical robot 100 may include a display 110, upper arm 102, lower arm 104, end-effector 112, vertical column 312, casters 314, a table 318, and ring 324 which uses lights to indicate statuses and other information. Cabinet 106 may house electrical components of surgical robot 100 including, but not limited, to a battery, a power distribution module, a platform interface board module, and a computer. The camera tracking system 200 may include a display 36, tracking cameras 204, arm(s) 202, a computer housed in cabinet 330, and other components.

In computer-assisted navigated surgeries, perpendicular 2D scan slices, such as axial, sagittal, and/or coronal views, of patient anatomical structure are displayed to enable user visualization of the patient's anatomy alongside the relative poses of surgical instruments. An XR headset or other display can be controlled to display one or more 2D scan slices of patient anatomy along with a 3D graphical model of anatomy. The 3D graphical model may be generated from a 3D scan of the patient, e.g., by a CT scan device, and/or may be generated based on a baseline model of anatomy which isn't necessarily formed from a scan of the patient.

Example Surgical System

FIG. 4 illustrates a block diagram of a surgical system that includes an XR headset 150, a computer platform 400, imaging devices 420, and a surgical robot 100 which are configured to operate according to some embodiments.

The imaging devices 420 may include a C-arm imaging device, an O-arm imaging device, and/or a patient image database. The XR headset 150 provides an improved human interface for performing navigated surgical procedures. The XR headset 150 can be configured to provide functionalities, e.g., via the computer platform 400, that include without limitation any one or more of: identification of hand gesture based commands, display XR graphical objects on a display device 438 of the XR headset 150 and/or another display device. The display device 438 may include a video projector, flat panel display, etc. The user may view the XR graphical objects as an overlay anchored to particular real-world objects viewed through a see-through display screen. The XR headset 150 may additionally or alternatively be configured to display on the display device 438 video streams from cameras mounted to one or more XR headsets 150 and other cameras.

Electrical components of the XR headset 150 can include a plurality of cameras 430, a microphone 432, a gesture sensor 434, a pose sensor (e.g., inertial measurement unit ("IMU")) 436, the display device 438, and a wireless/wired communication interface 440. The cameras 430 of the XR headset 150 may be visible light capturing cameras, near infrared capturing cameras, or a combination of both.

The cameras 430 may be configured to operate as the gesture sensor 434 by tracking for identification user hand gestures performed within the field of view of the camera(s) 430. Alternatively, the gesture sensor 434 may be a proximity sensor and/or a touch sensor that senses hand gestures performed proximately to the gesture sensor 434 and/or senses physical contact, e.g., tapping on the sensor 434 or its enclosure. The pose sensor 436, e.g., IMU, may include a multi-axis accelerometer, a tilt sensor, and/or another sensor that can sense rotation and/or acceleration of the XR headset 150 along one or more defined coordinate axes. Some or all of these electrical components may be contained in a head-worn component enclosure or may be contained in another enclosure configured to be worn elsewhere, such as on the hip or shoulder.

As explained above, a surgical system includes the camera tracking system 200 which may be connected to a computer platform 400 for operational processing and which may provide other operational functionality including a navigation controller 404 and/or of an XR headset controller 410. The surgical system may include the surgical robot 100. The navigation controller 404 can be configured to provide visual navigation guidance to an operator for moving and positioning a surgical tool relative to patient anatomical structure based on a surgical plan, e.g., from a surgical planning function, defining where a surgical procedure is to be performed using the surgical tool on the anatomical structure and based on a pose of the anatomical structure determined by the camera tracking system 200. The navigation controller 404 may be further configured to generate navigation information based on a target pose for a surgical tool, a pose of the anatomical structure, and a pose of the surgical tool and/or an end effector of the surgical robot 100, where the steering information is displayed through the display device 438 of the XR headset 150 and/or another display device to indicate where the surgical tool and/or the end effector of the surgical robot 100 should be moved to perform the surgical plan.

The electrical components of the XR headset 150 can be operatively connected to the electrical components of the computer platform 400 through the wired/wireless interface 440. The electrical components of the XR headset 150 may be operatively connected, e.g., through the computer platform 400 or directly connected, to various imaging devices 420, e.g., the C-arm imaging device, the I/O-arm imaging device, the patient image database, and/or to other medical equipment through the wired/wireless interface 440.

The surgical system may include a XR headset controller 410 that may at least partially reside in the XR headset 150, the computer platform 400, and/or in another system component connected via wired cables and/or wireless communication links. Various functionality is provided by software executed by the XR headset controller 410. The XR headset controller 410 is configured to receive information from the camera tracking system 200 and the navigation controller 404, and to generate an XR image based on the information for display on the display device 438.

The XR headset controller 410 can be configured to operationally process frames of tracking data from tracking cameras from the cameras 430 (tracking cameras), signals from the microphone 1620, and/or information from the pose sensor 436 and the gesture sensor 434, to generate information for display as XR images on the display device 438 and/or as other for display on other display devices for user viewing. Thus, the XR headset controller 410 illustrated as a circuit block within the XR headset 150 is to be understood as being operationally connected to other illustrated components of the XR headset 150 but not necessarily residing within a common housing or being otherwise transportable by the user. For example, the XR headset controller 410 may reside within the computer platform 400 which, in turn, may reside within the cabinet 330 of the camera tracking system 200, the cabinet 106 of the surgical robot 100, etc.

Figure 6:
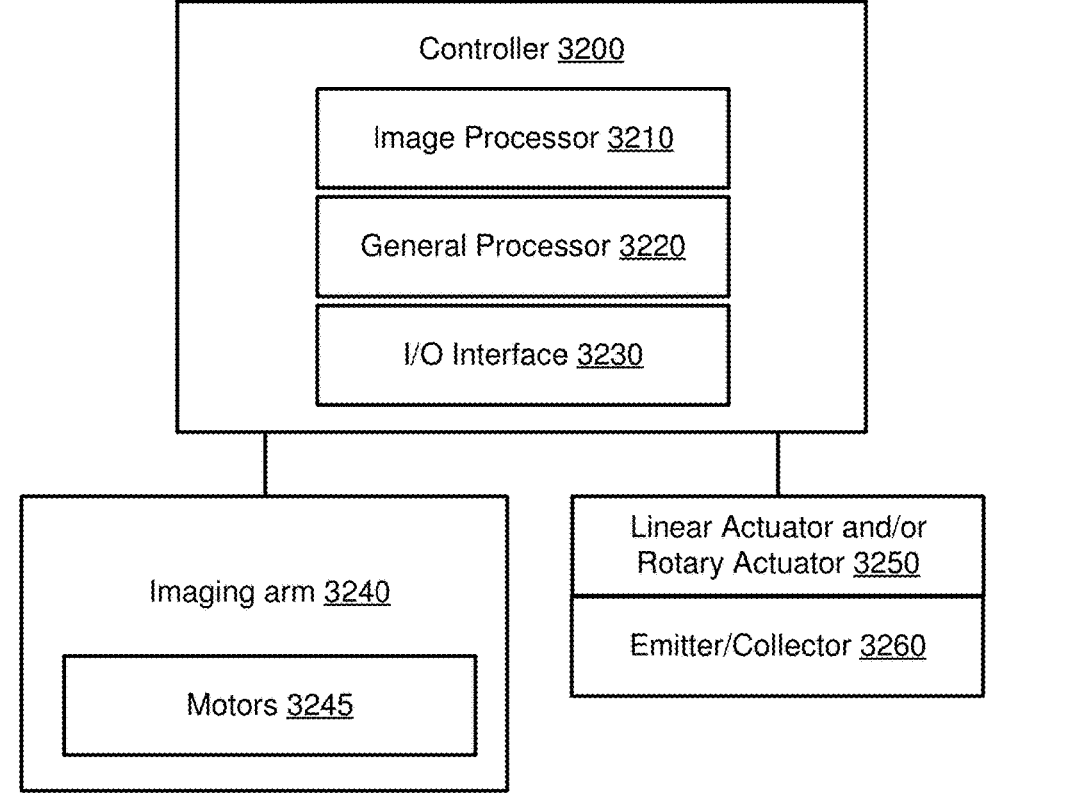
FIG. 6 is a block diagram illustrating an example of an imaging system according to some embodiments.

FIG. 6 illustrates a block diagram of components of a medical imaging system configured in accordance with some embodiments of the present disclosure. The medical imaging system includes a controller 3200, a imaging arm 3240 (e.g., a C-arm or an O-arm), a linear actuator and/or rotary actuator 3250 connected to an X-ray beam emitter or collector 3260. The controller 3200 includes an image processor 3210, a general processor 3220, and an I/O interface 3230. The image processor 3210 performs image processing to combine sets of images to generate a three-dimensional image of the scanned volume. The general processor 3220 is used to perform various embodiments of the present disclosure. The I/O interface 3230 communicatively couples the controller 3200 to other components of the medical imaging system. The imaging arm 3240 includes motors 3245 used to move the collector and emitter along an arc, e.g., three hundred and sixty degrees, during image acquisition. Motors 3245 are controlled by C-arm the controller 3200. The controller 3200 can also control movement of the linear actuator and/or rotary actuator 3250.

Figure 7A:
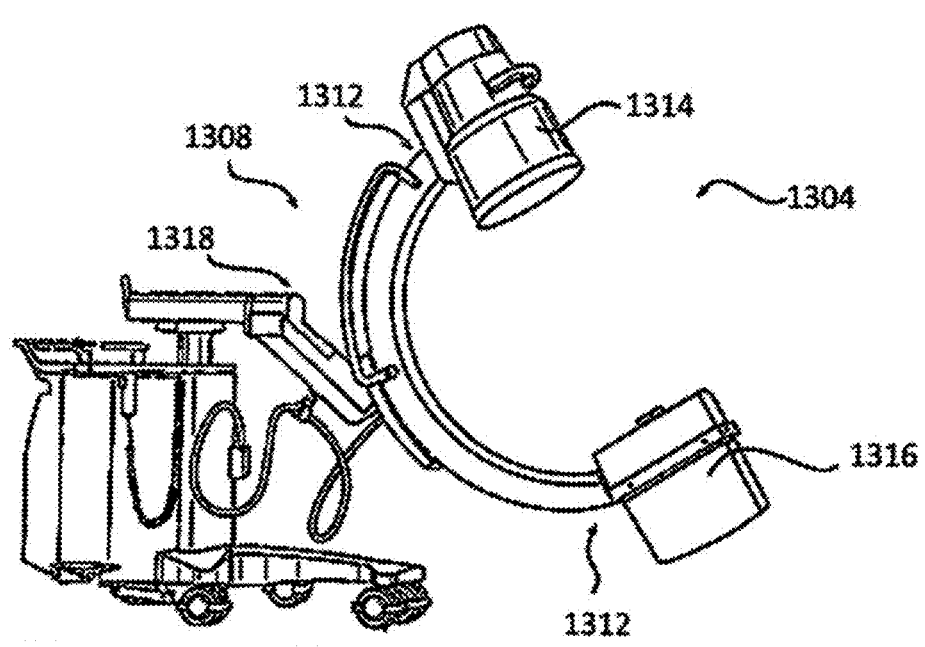
FIGS. 7A-B are schematic diagrams illustrating examples of imaging devices according to some embodiments.
Figure 7B:
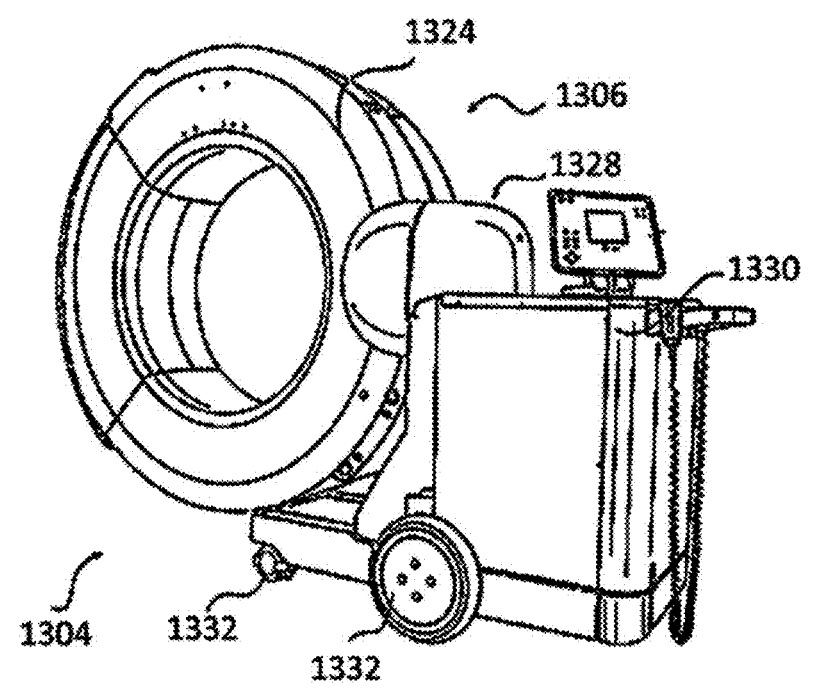

FIGS. 7A-B illustrate medical imaging systems 1304 that may be used in conjunction with robot system 100 and/or navigation systems to acquire pre-operative, intra-operative, post-operative, and/or real-time image data of patient 210. Any appropriate subject matter may be imaged for any appropriate procedure using the imaging system 1304. The imaging system 1304 may be any imaging device such as a C-arm 1308 device, an O-arm 1306 device, a fluoroscopy imaging device, a magnetic resonance imaging scanner, etc. It may be desirable to take x-rays of patient 210 from a number of different positions, without the need for frequent manual repositioning of patient 210 which may be required in an x-ray system. As illustrated in FIG. 7A, the imaging system 1304 may be in the form of a C-arm 1308 that includes an elongated C-shaped member terminating in opposing distal ends 1312 of the "C" shape. C-shaped member 1130 may further comprise an x-ray source 1314 and an image receptor 1316. The space within C-arm 1308 of the arm may provide room for the physician to attend to the patient substantially free of interference from x-ray support structure 1318. As illustrated in FIG. 7B, the imaging system 1304 may include an O-arm imaging device 1306 having a gantry housing 1324 attached to a support structure imaging device support structure 1328, such as a wheeled mobile cart 1330 with wheels 1332, which may enclose an image capturing portion, not illustrated. The image capturing portion may include an x-ray source and/or emission portion and an x-ray receiving and/or image receiving portion, which may be disposed about one hundred and eighty degrees from each other and mounted on a rotor (not illustrated) relative to a track of the image capturing portion. The image capturing portion may be operable to rotate three hundred and sixty degrees during image acquisition. The image capturing portion may rotate around a central point and/or axis, allowing image data of patient 210 to be acquired from multiple directions or in multiple planes. Although certain imaging systems 1304 are exemplified herein, it will be appreciated that any suitable imaging system may be selected by one of ordinary skill in the art.

Interpolation and Latent Spaces are described below.

Traditional algorithmic techniques for interpolating digital signals include: linear or polynomial interpolation, transforming the signal into a different space by transforms (e.g., the Discrete Fourier Transform ("DFT") or Discrete Wavelet Transform ("DWT")), and appending zeros and performing inverse transforms. These models assume that the digital signal can be expressed in terms of a number of parameters, which are computed using known underlying characteristics of the signal. Neural networks have also been applied for such computations by training a model to predict how data of particular patterns surrounding the area to be interpolated should be combined to produce the desired appearance.

However, none of these techniques yields satisfactory results in regards to medical imaging because the underlying continuous-bandlimited spatial function (e.g., the physical object being imaged), has been truncated by a limited aperture of an imaging system. Therefore, the spatially truncated image has infinite bandwidth. Moreover, the Nyquist Sampling Theorem in its basic form is an infinite sum, which means, even for the truly bandlimited function (which must necessarily have infinite spatial extent), requires an infinite number of samples for its faithful reconstruction. This requirement can never be met by any real imaging system. Therefore, there is a limited ability to increase the spatial resolution of medical images with existing interpolation, and any attempt that appears to improve the spatial resolution of these images introduces artifacts or inconsistencies.

Examples are provided below to illustrate the limitations involved in interpolating medical images.

In some examples, two images are provided: a first image of a cat and a second image of the same cat that is a rotated version of the first image. To a human, these two images are identical (albeit one is rotated) and represent the same object (the same cat). From an Information Theory point of view, these images are also identical (e.g., the images have the same entropy and same distribution of the pixel intensities). However, an attempt to interpolate a third picture from the first image and second image (e.g., by interpolating between the pixel values) would likely result in something that has nothing to do with either image. Indeed, to an interpolation procedure, the original cat image and its rotated version are very different from each other (e.g., in a L2 sense).

In another example, two images are provided: a first image of a cat and a second image that is a blurred or noisy version of the first image (in the same orientation). An attempt to interpolate a third image based on the first image and the second image may be much less dissimilar than the interpolation in the previous example. Indeed, for reasonably small or medium noise levels, some or all interpolated images may look reasonably good. As the noise level is increased, the quality of interpolated images degrades linearly/continuously. This degradation is in sharp contrast to the previous case where the majority of interpolated images are unrecognizable even for small rotations of the two images.

In some examples, in order to perform meaningful interpolation between images, the latent space (e.g., where similar images are close to one other) must be discovered. Some Deep Learning image classification systems project an input into the latent space where the system has established boundaries for various classes. The label for a particular input can be deduced by where it lands in that latent space. It is this latent space where interpolation can be performed effectively. The two images of a cat and its rotated version are next door neighbors in the latent space. The noisy versions of the same image are not too far either as will be discussed shortly.

There does not exist a unique latent space. Instead, it is constructed on a case by case basis to solve the problem at hand. For example, the dimension of the latent space of a collection of Gaussian random variable depends on the number of eigen vectors retained after performing the eigen value decomposition of the covariance matrix, which has to be decided based on the specific requirements of the problem being solved. However, discovering the latent space always entails compression or dimensionality reduction. The compression algorithm, necessarily gets rid of noise and superfluous information (e.g. rotated or noisy images of cats) to achieve its goal. To give an example, consider the population of the planet earth. Each person looks very different as they may be rich or poor, driving expensive luxury car, etc. However, the same people would look more similar on the beach after all the extra particularities of the individuals have been stripped away.

Content and Style Vectors are described below.

In Deep Learning, this compression (for images) is achieved using the Convolutional Neural Networks ("CNN"). CNNs, by the way of their construction, summarize their input into what is known as feature maps. Feature maps include information about what things are in the input image as opposed to where things are. For example, a feature map produced by a trained CNN to classify cats (yes/no) may include information about existence of pointed ears, etc. However, it does not contain information about where the pointed ears may be. So, feature maps produced from an image of a cat and its rotated version include very similar information. The same is also true for the images of a cat and its noisy version. These feature maps are the original definition of what is called the "content". The CNN extracts the "content" by repeatedly eroding and under-sampling its input.

One way to recover a meaningful image from the interpolated but compressed latent space representation is to decompress it and try to recover a full-size image. Unfortunately, when this decompression is done, the quality of the recovered images is not very good. The reason is that the compression algorithm may leave holes in the latent space. Plus, the compression is lossy and some information is ultimately lost. This is where the variational methods come in where they try to fit statistics of the latent space into a particular distribution. Variational decoders do a better job of recovering of these images. A second method involves defining a "style" vector where extra vital information about an image may be stored. This vector includes information about the way an image looks. It defines the spatial correlation of various pieces of the "content" vector. The "style" is the Gramian matrix of the feature maps collected at various layers of a CNN that has been trained for image classification. In some examples, "content" can be "where things are" and "style" can be "what things look like."

The ideas described above are part of a branch of Deep Learning called the Neural Style Transfer ("NST"). In some examples, NST include the following operations: (1) Obtain a pre-trained Convolutional Neural network for image classification. Discard the classification part and retain only the feature extraction parts. (2) Use this network to compute the style vector of the style image and save. (3) Use this network to compute the content of the content image and save. (4) Freeze the weights and biases of this network. (5) Use an image including noise samples as input and compute the cost function, which uses the content and style of the noise image and the vectors saved in (2) and (3). (6) Use the back propagation (the weights are frozen) to manipulate the current input image to minimize the cost. At the end of the optimization, a stylized image is obtained. Note that this process does not involve training a Neural Network explicitly. A newer approach accomplishes this training using Generative Adversarial Networks, Encoders, and Decoders as discussed in this document.

Figure 8:
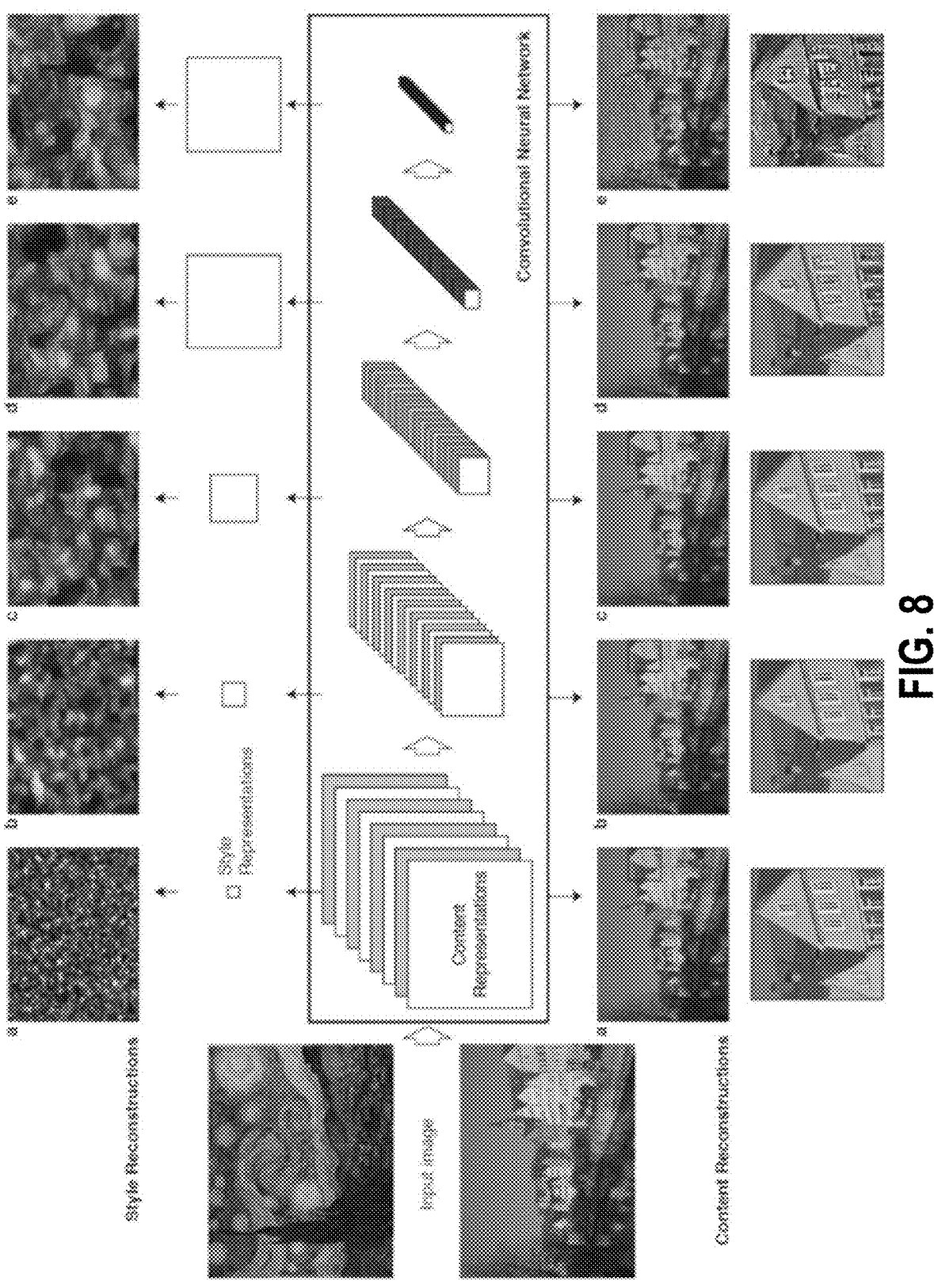
FIG. 8 is a diagram illustrating an example of generating an image based on a content vector and a style vector according to some embodiments.

An example of NST is illustrated in FIG. 8. A content image (e.g., the picture of houses in FIG. 8) is taken along with another picture known as the style image (e.g., the "Starry Night" paining in FIG. 8). The content and the style vectors of the two images are then extracted. These two vectors are used to morph noise into an image that has the content of the content image but the style of the style image. The latter stage performed is pure optimization and no CNN training is required as all the weights and biases of the CNNs are frozen.

Figure 9:
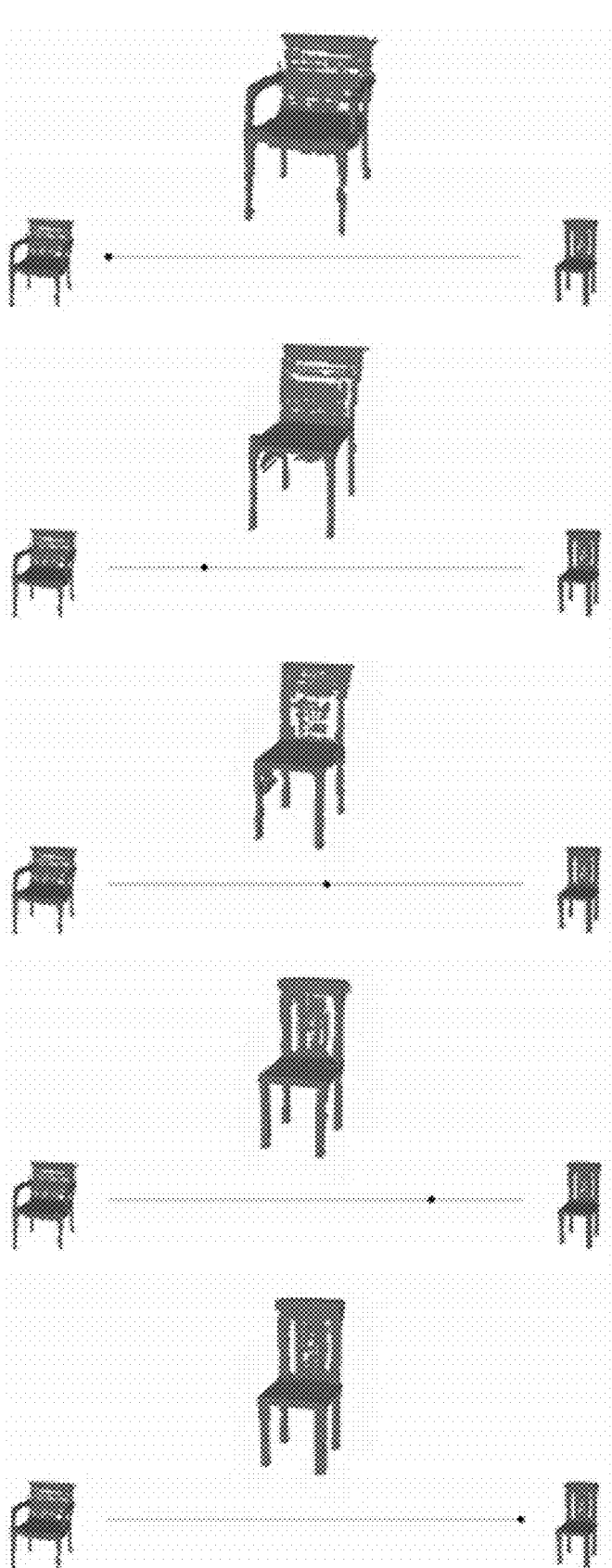
FIG. 9 is a diagram illustrating examples of an interpolated image of a chair based on assigning different weights to two different content vectors according to some embodiments.

The techniques used in NST can be used to generate new images by interpolating the content vectors of two reasonably close images. The image sequence illustrated in FIG. 9 shows how the two original chairs are morphed into an image that is an amalgamation of the two chairs.

The NST algorithm briefly described above may not be satisfactory for many real applications, in particular for medical imaging application where contrast and fidelity of the images produced is of utmost importance.

Interpolation Using Neural Networks is described below.

Medical images of a spine or a brain usually have similar styles for similar modality (e.g., all brains look roughly the same). The content, however, does change. Interpolation may be used to handle lower resolution along one dimension of a volume, such as the lower resolution of slice dimension for a magnetic resonance imaging ("MRI") volume vs. higher resolution within each slice as shown in FIG. 10.

Figure 10:
FIG. 10 is an image illustrating an example of a reconstructed volume from a magnetic resonance ("MRI") imaging scan according to some embodiments.

FIG. 10 illustrates the reconstructed volume from a MRI with modality synthesis to create a computed tomography ("CT")-like appearance in diagonal tiles of a checkerboard layout using a set of sagittal slices. Sagittal plane resolution is high (<1 mm, right). However, because the inter-slice distance is large (~5 mm) the resolution in axial and coronal views (left) is poor.

In some embodiments, to accomplish interpolation, a neural network can be trained to create content and style vectors from an image volume dataset. One trick to drive separation of content and style vectors is to use different transforms (slightly cropped, rotated, translated) of the same image and make sure the resulting style vectors are similar and the content vectors change. Such a network can include two sub-networks: an encoder network and a decoder network. The encoder network can use images as input and generate a content vector and a style vector as output. The decoder network can use a content vector and a style vector to create images as output.

In some embodiments an image can be interpolate from two images using a set of operations. The operations include using the encoder to generate a content vector and a style vector for a first image. The style vector can then be discarded. The operations can further include using the encoder to generate a content vector and a style vector for a second image. Again, the style vector can then be discarded. The operations can further include generating a new content vector by interpolating the content vectors (from the first image and the second image). The operations can further include using a decoder to generate an interpolated image based on the new content vector, and a globally optimized style vector. In some examples, the globally optimized style vector refers to a predetermined style vector that optimizes the performance of certain downstream image processing algorithms such as semantic image segmentation or presentation of image view to the user.

Figures 11A, 11B, 11C:
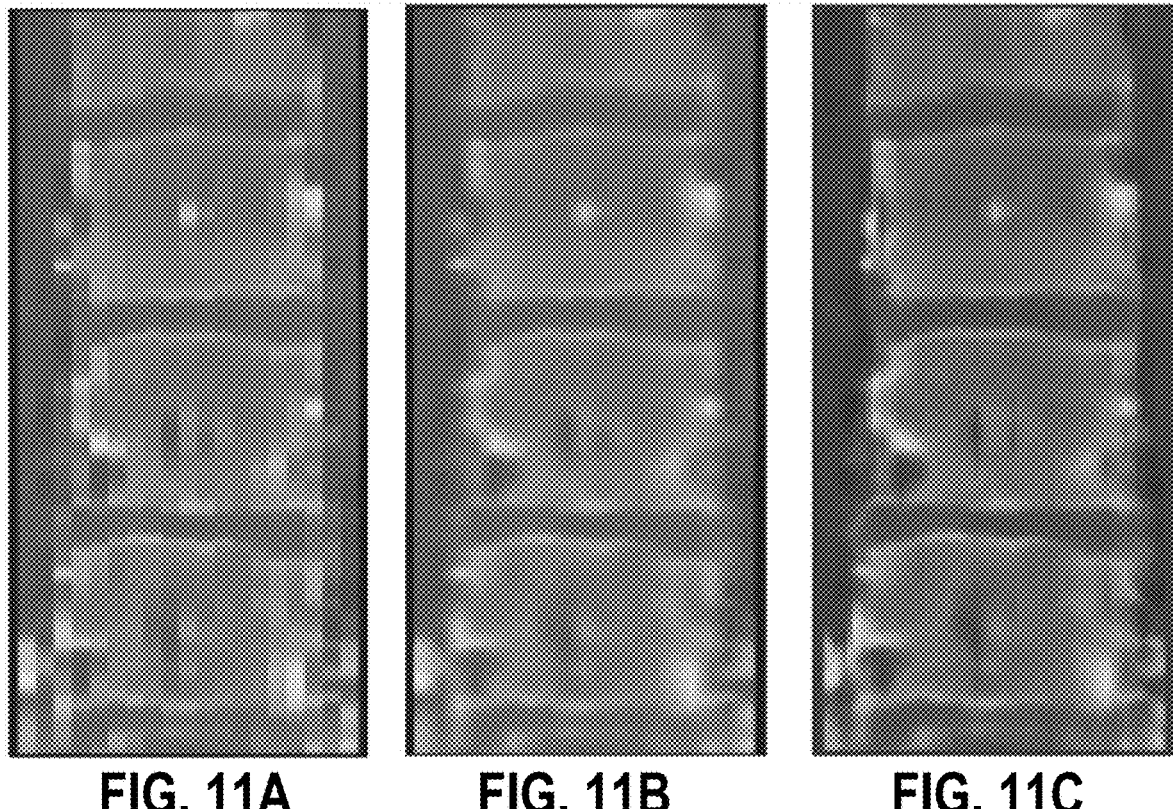
FIGS. 11A-C are examples of images of a spine produced from a CT scan using different procedures according to some embodiments.

FIGS. 11A-C illustrate an example of different images generated based on a CT scan. FIG. 11A is an example of an image directly from the CT scan. FIG. 11B is an example of an image generated using linear interpolation of two images taken during the CT scan. FIG. 11C is an example an image generated using content interpolation (as described in the above embodiments) of content vectors extracted from two images taken during the CT scan.

Figure 12:
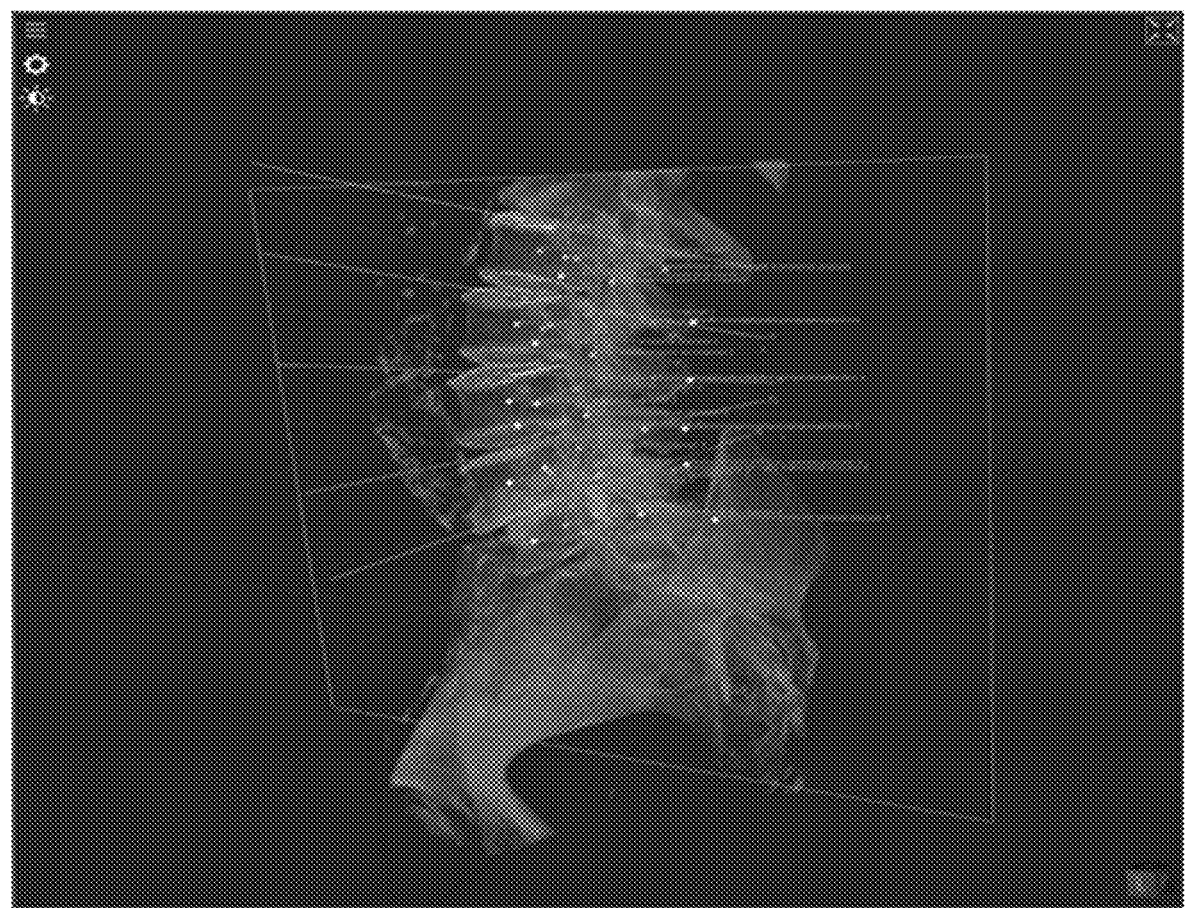
FIG. 12 is an image illustrating an example of an interpolated medical image with segmentation and labeling using a style vector according to some embodiments.

FIG. 12 is an example of an interpolated image of a spine in which a style vector was used to segment and label parts of the spine. In some examples, the neural networks are trained to look for features/contrast in 3D voxels to effectively label voxels as belonging to a vertebral level. The image in FIG. 12 illustrates several vertebrae segmented, with the edges highlighted.

In some embodiments, the image interpolation has potential applications in areas of robotic assisted surgery. In some examples, image interpolation can be used with fluoroscopy shots (X-rays) of anatomy from different positions of emitter and detector. Fluoroscopy is commonly used in operating rooms ("OR") for real-time navigation of implants and instruments. For proper visualization, a view that shows key anatomical features, such as end plate of a vertebra, is desired. Such a view needs the emitter and detector of the C-Arm to be physically aligned with the anatomical feature. This alignment is often difficult to guess. The user typically takes multiple fluoroscopy images by making a rough guess of the alignment and then slightly adjusting the orientation of C-Arm until the desired image is produced. Using the content-based interpolation described in some embodiments, only two fluoroscopy images may be needed. Images can be produced by finely interpolating the space in-between the original images where the desired key feature may be seen. In some examples, a key feature of a anatomy is best viewed when the X-ray images are taken at 53.4 degrees (with respect to some origin). It may not be possible to guess this setting precisely. An experienced technician may guess that the setting should be 52 degrees. Once the desired key feature is not clearly observed, he/she may change the setting to 54 degrees. Once again, the sought-after feature may not be observed clearly. The two images can then be interpolated every tenth of a degree so that the desired key feature can be observed in one of the interpolated images.

In additional or alternative embodiments, content-based interpolation can be used with fluoro shots of anatomy that are used for CT reconstruction (e.g., shots along a circular path from the O-arm). Currently, a three-dimensional CT scan is created using the back-projection algorithm where the X-rays taken at various angles and spacings (e.g., one degree apart) are processed to produce the required 3D volume. In some examples, it is possible to use a larger angular space between the X-rays (e.g., two degrees apart) and produce a 3D scan at lower resolution, which reduces the scan time and X-ray exposure to the patient. A higher resolution 3D scan may then be produced by interpolation as described above.

In some embodiments, the content is the view from each perspective and the style is the same from all perspectives or a globally optimized style vector. By knowing the temporal or spatial location of each view, intermediate views can be computed by using some style vector and interpolated content vectors as discussed above.

For a completely new system model, the same technique can be extended to use an untrained network. That is, each dataset can be treated as training data to compute constant style vector and changing content vectors. The content vectors are then interpolated and combined with constant style vector to yield an interpolated dataset. For example, a full-dose x-ray could be taken of a patient, followed by a low-dose x-ray. These data would be used as constant style and changing content training data. Then, all subsequent x-rays could be taken at low dose and the training data used to impart the style of a full dose x-ray on the low-dose x-rays taken using different content (orientation).

In some embodiments, using content-based interpolation to generate medical images can result in improved resolution of radiological images along direction of low resolution.

In additional or alternative embodiments, using content-based interpolation to generate medical images can result in reduced time and radiation dose to find optimal fluoroscopy image in OR.

In additional or alternative embodiments, using content-based interpolation to generate medical images can result in reduced radiation dose by digitally interpolating x-ray images for CT reconstruction.

Figure 14:
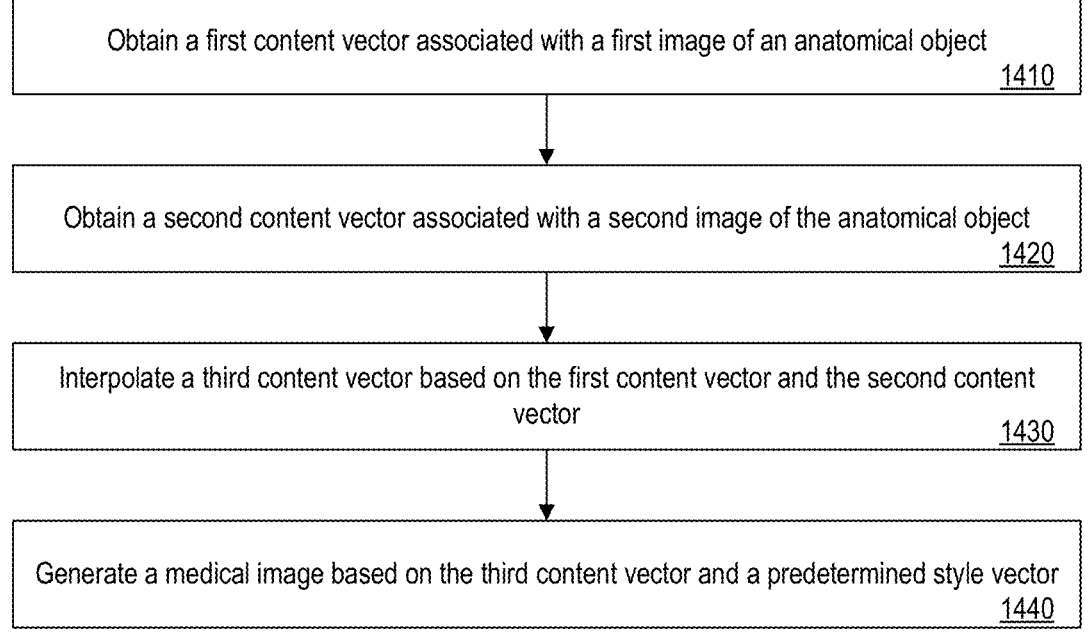

FIGS. 13-14 illustrate operations performed by a system to interpolate an image. Although the flow charts of FIGS. 13-14 are described below in regards to the imaging system of FIG. 6, the operations may be preformed by any suitable system.

FIG. 13 illustrates operations performed by a system to generate an image of an object.

At block 1310, processor 1320 determines information associated with objects based on a feature of an object that is desired to be illustrated in an interpolated image. In some embodiments, the objects are anatomical objects and the object is a specific anatomical object of a person. In some examples, the information includes characteristics that are generally present in images of the objects. In additional or alternative examples, the information includes data to cause an interpolated image of the object to be of a certain style (e.g., segmented or labeled) to better illustrate a feature of the object. In additional or alternative embodiments, the information is referred to as a style vector (or more specifically a globally-optimized style vector). In some examples, the term globally-optimized style vector refers to a style vector that has been trained by a machine learning procedure based on a plurality of images.

At block 1320, processor 1320 obtains a first image of the object. In some embodiments, obtaining the first image includes capturing (e.g., via a camera or an x-ray detector) the first image.

At block 1330, processor 1320 extracts first information associated with the object from the first image. In some embodiments, extracting the first information includes generating, using an encoder, a first content vector based on the first image.

At block 1340, processor 1320 obtains a second image of the object. In some embodiments, obtaining the second image includes capturing (e.g., via a camera or an x-ray detector) the second image.

At block 1350, processor 1320 extracts second information associated with the object from the second image. In some embodiments, extracting the second information includes generating, using an encoder, a second content vector based on the second image.

At block 1360, processor 1320 generates third information associated with the object based on the first information and the second information. In some embodiments, the first image is an image of the object from a first position and a first pose and the second image is an image of the object from a second position and a second pose, the second position being different than the first position and/or the second pose being different than the first pose. Generating the third information includes: generating a plurality of interpolations between the first information and second information, each interpolation of the plurality of interpolations being generated based on assigning a different weight to the first information relative to the second information; and selecting an interpolation of the plurality of interpolations as the third information based on a feature of the object being represented better by the interpolation than another interpolation of the plurality of interpolations.

At block 1370, processor 1320 generates an interpolated image of the object based on the third information and predetermined information (from block 1310). In some embodiments, the first information, second information, and third information each include an attribute of a characteristic of the object, and the predetermined information includes characteristics of the objects.

In additional or alternative embodiments, generating the interpolated image includes generating a plurality of interpolated images, each interpolated image of the plurality of interpolated images generated based on one interpolation of a plurality of interpolations; and selecting the interpolated image from the plurality of interpolated images based on the interpolated image illustrating a feature of the object better than other interpolated images in the plurality of interpolated images.

At block 1380, processor 1320 uses the interpolated image. In some embodiments, using the interpolated image includes at least one of: displaying the interpolated image; providing the interpolated image to a robotic surgery system; and generating a three-dimensional model of the object based on the interpolated image.

FIG. 14 illustrates operations performed by a medical imaging system to generate a medical image. At block 1410, processor 1320 obtains a first content vector associated with a first image of an anatomical object. At block 1420, processor 1320 obtains a second content vector associated with a second image of an anatomical object. At block 1430, processor 1320 interpolates a third content vector based on the first content vector and the second content vector. At block 1440, processor 1320 generates a medical image based on the third content vector and a predetermined style vector.

Various operations of FIGS. 13-14 may be optional.

Further Definitions and Embodiments

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/ operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, microcode, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the appended examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the following examples of embodiments and their equivalents, and shall not be restricted or limited by the foregoing detailed description.

What is claimed is:

1. A system configured to generate a medical image, the system comprising:
  a neural network pre-trained with a set of images containing internal tissue of an anatomical object of a plurality of patients, the neural network including:
    a pre-trained encoder configured to receive an input image and generate a content vector as an output, the content vector representing what features of the anatomical object are present in the input image; and
    a pre-trained decoder configured to receive the content vector to generate an interpolated image as an output;
  processing circuitry coupled to the neural network; and
  memory coupled to the processing circuitry and having instructions stored therein that are executable by the processing circuitry to cause the system to perform operations including:
    obtaining a first two-dimensional image of an anatomical object;
    using the encoder, extracting first information associated with the anatomical object from the first image, the first information containing the content vector of the first image;
    obtaining a second two-dimensional image of the anatomical object;
    using the encoder, extracting second information associated with the anatomical object from the second image, the second information containing the content vector of the second image;
    interpolating the first and second information to generate an interpolated content vector;
    using the decoder, generating the medical image based on the interpolated content vector.

2. The system of claim 1, wherein the first information and second information each include an attribute of a characteristic of the anatomical object, and wherein the predetermined information includes characteristics of the anatomical objects.

3. The system of claim 1, the operations further comprising:
  interpolated content vector and the predetermined information that is associated with images of anatomical objects of a type that is a type of the anatomical object.

4. The system of claim 3, wherein the first image is an image of the anatomical object from a first position and a first pose, wherein the second image is an image of the anatomical object from a second position and a second pose, the second position being different than the first position and/or the second pose being different than the first pose, wherein interpolating includes:

generating a plurality of interpolations between the first information and second information, each interpolation of the plurality of interpolations being generated by assigning a different weight to the first information relative to the second information; and selecting an interpolation of the plurality of interpolations as the interpolated content vector based on a feature of the anatomical object being represented better by the interpolation than another interpolation of the plurality of interpolations.

5. The system of claim 3, wherein the predetermined information includes a globally-optimized style vector, the style vector representing where the features are located in the input image.

6. The system of claim 3, the operations further comprising:

determining the predetermined information based on a feature of the object that is desired to be better illustrated in the medical image.

7. The system of claim 3, wherein the predetermined information includes an indication of a way of segmenting anatomical objects, highlighting portions of the anatomical object, and labeling parts of the anatomical object, and wherein the medical image includes a segmented version of the anatomical object, with portions of the anatomical object highlighted, and parts of the anatomical object labeled based on the predetermined information.

8. The system of claim 1, further comprising:

an x-ray detector coupled to the processing circuitry, wherein obtaining the first image includes capturing, by the x-ray detector, the first image, and wherein obtaining the second image includes capturing, by the x-ray detector, the second image.

9. The system of claim 1, the operations further comprising at least one of:

displaying the medical image;

providing the medical image to a robotic surgery system.

10. A system configured to generate a medical image, the system comprising:

a neural network pre-trained with a set of non-optical images containing an anatomical object of a plurality of patients, the neural network including:

a pre-trained encoder configured to receive an input image and generate a content vector as an output, the content vector representing what features of the anatomical object are present in the input image; and a pre-trained decoder configured to receive the content vector to generate an interpolated image as an output;

processing circuitry coupled to the neural network; and memory storing the neutral network and coupled to the processing circuitry, the processing circuitry programmed to execute the following instructions:

obtaining a first non-optical image of an anatomical object containing internal features under a skin;

using the pre-trained encoder of the neural network, extracting the content vector associated with the anatomical object from the first image;

obtaining a second non-optical image of the anatomical object containing internal features under a skin;

using the pre-trained encoder of the neural network, extracting second information associated with the anatomical object from the second image, the second information containing the content vector of the second image;

interpolating the first and second information to generate an interpolated content vector;

using the pre-trained decoder of the neural network, generating the medical image based on the interpolated content vector.

11. The system of claim 10, wherein the first and second images are 2-dimensional x-ray images and the generated medical image is an x-ray image which has been interpolated from the first and second x-ray images.

12. The system of 11, the processing circuitry further programmed to execute the following instructions:

repeating the instructions of generating the medical image for M sets of first and second images to generate N medical images;

using the N sets of first and second images and N medical images, generating a 3-dimensional CT image for purposes of reducing x-ray exposure to the patient.

* * * * *